United States Patent [19]
Yan

[11] Patent Number: 6,066,779
[45] Date of Patent: May 23, 2000

[54] CROP HETEROSIS AND HERBICIDE

[75] Inventor: Wengui Yan, Stuttgart, Ark.

[73] Assignee: Yan's Heterosis & Herbicide, Inc., Stuttgart, Ark.

[21] Appl. No.: 09/067,489

[22] Filed: Apr. 27, 1998

Related U.S. Application Data

[60] Provisional application No. 60/044,990, Apr. 28, 1997, and provisional application No. 60/046,058, May 9, 1997.

[51] Int. Cl.⁷ ..................................................... A01H 1/00
[52] U.S. Cl. ........................... 800/274; 435/430; 800/278; 800/279; 800/300; 800/303; 800/320; 800/320.2
[58] Field of Search ............................ 435/430; 800/274, 800/278, 279, 300, 303, 320, 320.2

[56] References Cited

U.S. PATENT DOCUMENTS

| | | | |
|---|---|---|---|
| 3,955,959 | 5/1976 | Skipper | 71/118 |
| 4,168,963 | 9/1979 | Rupp et al. | 71/86 |
| 4,305,225 | 12/1981 | Yuan | 47/58 |
| 4,351,130 | 9/1982 | Rutger et al. | 47/58 |
| 4,400,196 | 8/1983 | Albrecht et al. | 71/86 |
| 4,658,085 | 4/1987 | Beversdorf et al. | 800/1 |
| 4,764,643 | 8/1988 | Calub | 800/1 |
| 4,839,231 | 6/1989 | Vandekerckhove | 428/441 |
| 5,180,873 | 1/1993 | Jorgensen | 800/205 |
| 5,290,690 | 3/1994 | Mrabet et al. | 435/17.3 |
| 5,310,665 | 5/1994 | Lambeir et al. | 435/94 |
| 5,356,799 | 10/1994 | Fabijanski et al. | 435/172.3 |
| 5,364,782 | 11/1994 | Quax et al. | 435/202 |
| 5,369,027 | 11/1994 | Lambert et al. | 435/252.2 |
| 5,376,536 | 12/1994 | Quax et al. | 435/100 |
| 5,409,823 | 4/1995 | Crossland et al. | 435/172.3 |
| 5,487,991 | 1/1996 | Vandekerckhove et al. | 435/172.3 |
| 5,545,822 | 8/1996 | Croughan | 800/235 |
| 5,550,318 | 8/1996 | Adams et al. | 800/205 |
| 5,589,610 | 12/1996 | De Beuckeleer et al. | 800/205 |
| 5,641,664 | 6/1997 | D'Halluin et al. | 435/172.3 |
| 5,659,123 | 8/1997 | Van Rie et al. | 800/205 |
| 5,679,558 | 10/1997 | Gobel et al. | 435/172.3 |
| 5,723,763 | 3/1998 | Mariani et al. | 800/205 |
| 5,750,867 | 5/1998 | Williams et al. | 800/205 |

OTHER PUBLICATIONS

Chuong et al., Somatic transfer of cytoplasmic traits in Brassica napus L. by haploid protoplast fusion, Mol. Gen. Genet., 211: 197–201, 1988.
Sankula et al., Genetic analysis of glufosinate resistance in crosses between transformed rice (*Oryza sativa*) and Red rice (*Oriza sativa*), Weed Technology, 12: 209–214, 1998.
Huang, Danian, Zhang Shanqing, XUE Rui, HUA Zhihua, XIE Xiaobo, and Wang Xiooling, CNRRI, Hangzhou 310006, China, A new method to identify and improve the purity of hybrid rice with herbicide resistant gene, *Chinese Rice Research Newsletter*, Mar. 1988, vol. 6, No. 1.
Hybrids Gain Consultants' Approval, Quantum Waves, Bringing New Energy To Wheat, Spring 1997.
Reynaerts et al., Engineered genes for fertility control and their application in hybrid seed production, *Scientia Horticulturae*, 55 (1993) 125–139.
Sankula Sujatha, Braverman Michael P., and Oard James H., Genetic Analysis of Glufosinate Resistance in Crosses Between Transformed Rice (*Oryza sativa*) and Red Rice (*Oryza sativa*), Weed Technology, 1998, vol. 12:209–214.
XIAO Guoying, The View of Crop Herbicide Resistance for Heterosis Utilization, Hybrid Rice, 1997, 12(5), Special Thesis.
Huang Danian, Zhang Shanqing, XUE Rui, HUA Zhihua, XIE Xiaobo, and Wang Xiaoling, A New Method to Identify and Improve the Purity of Hybrid Rice with Herbicide Resistant Gene, China National Rice Research Institute, Hangzhou 310006, China, Mar., 1998, vol. 6 No. 1.
Yuan Long–Ping, FU Xi–Qin, Technology of Hybrid Rice Production, Food and Agriculture Organization of the United Nations, Rome, 1995, pp. 69–77.
Rathore Keerti S., Chowdbury Vijay K., Hodges Thomas K., Use of Bar as a Selectable Marker Gene and for the Production of Herbicide–Resistant Rice Plants from Protoplasts, Plant Molecular Biology 1:871–884, 1993.
Denis M., Delourme R., Gourret J.P., Mariani C., Renard M., Expression of Engineered Nuclear Male Sterility in Brassica Napus. Genetics, Morphology, Cytology, and Sensitivity to Temperature, Plant–physiol. Rockville, MD: American Society of Plant Physiologists, 1926–Apr. 1993. V. 101(4), pp. 1295–1304.

*Primary Examiner*—Elizabeth F. McElwain
*Assistant Examiner*—Anne Marie Grünberg
*Attorney, Agent, or Firm*—Head, Johnson & Kachigian

[57] ABSTRACT

Heterosis designates the increased growth or other augmented action resulting from crossing, however it is produced. Male sterility of female parent is an important biological mechanism for the commercial production of hybrid seed. Male sterility can be created by genetic manipulation, environmental influences, chemical induction and biological engineering. In principle, male sterility is a physiological disorder and the creation of complete male sterility either is costly or brings about other physiological disorders. Integrating the resistance gene to a non-selective herbicide into male parent and spraying the herbicide onto the hybrid population resulting from mating with the male parent for securing hybrid purity reduce the strict demand for complete male sterility. Therefore, simple and practical methodologies such as environmental and chemical means can be employed in the induction of male sterility, and the conflict of male sterility with other physiological disorders can be well balanced. The concept of this invention is applicable to all the crops and plants in which male sterility has been studied for heterosis purposes including rice (*Oryza sativa* L.), wheat (*Triticum aestivum* L.), corn (*Zea mays* L.), cotton (*Gossypium hirsutum* L.), soybean (*Glycine max* L.), sorghum [*Sorghum bicolor*(L.) Moench], rapeseed (*Brassica napus* L.), barley (*Hordeum vulgare* L.), oat (*Avena sativa* L.), rye (*Secale cereale* L.), pearl millet [*Pennisetum typhoides* (Burm) Stspf et Hubb.], alfalfa (*Medicago sativa* L.), tomato (*Lycopersicon esculentum* L.), sugar beet (*Beta vulgaris* L.), sunflower (*Helianthus annuus* L.), onion (*Allium cepa* L.), petunia (*Petunia hybrida* Hort.), and carrot (*Daucus carota* L.).

29 Claims, 7 Drawing Sheets

CROP HETEROSIS AND HERBICIDE

CROSS REFERENCE TO RELATED APPLICATIONS

Priority is claimed to and this application is a continuation-in-part of U.S. provisional application Ser. No. 60/044,990, filed Apr. 28, 1997, which is hereby incorporated by reference. Priority is claimed to and this application is also a continuation-in-part of U.S. provisional application Ser. No. 60/046,058, filed May 9, 1997, which is hereby incorporated by reference.

This application is also a continuation-in-part of Chinese application Serial No. 97 1 07807.6, filed Dec. 5, 1997.

REFERENCE TO A MICROFICHE APPENDIX

Not applicable.

BACKGROUND OF THE INVENTION

The present invention is directed to the breeding of crops or plants to produce hybrids having increased vigor or other superior qualities arising from the cross breeding of genetically different male and female plants or crops. More particularly, the present invention is directed to crop or plant heterosis involving a female parent which is male sterile and a male parent which is male fertile and contains a herbicide resistant gene to produce hybrid seeds, plants and crops which are subjected to a non-selective herbicide in order to kill or eliminate all non-pure hybrids or plants that were not from crossing with the transgenic male parent.

Herbicide and Herbicide-Resistant Crops

Herbicides are phytotoxins used by humans to kill unwanted vegetation. The compounds can be completely nonselective, killing every species of plant, or very selective, killing only certain plants. Several hundred herbicide active ingredients have been developed since the dawn of chemical control of weeds in the 1940's. The mechanisms of action of most of these compounds are known (Pilmoor et al., 1995), although there are still many gaps in our knowledge. Most herbicides are thought to directly affect only one molecular target in the plant, resulting in a cascade of secondary and tertiary effects that eventually kill the plant. Control of weeds with herbicides has been critical in food production because weeds compete with crops for water, nutrients, and soil. In addition, weeds can harbor insect and disease pests, and noxious weeds and weed seeds can greatly undermine crop quality. For these reasons, close to 100% of the U.S. corn, rice and soybean acres are treated with herbicides (Gianessi and Puffer, 1991).

Biotechnology may alter our future in many ways. One is by altering crop species to provide new traits that have been impossible or very slow to produce by conventional breeding. Imparting herbicide resistance to normally herbicide-susceptible crops to produce herbicide-resistant crops (HRCs) has been one of the most intensively exploited area of plant biotechnology. The progress achieved in the genetic manipulation of plants and the ability to transfer genetic information from any source organism has opened up an exciting and productive area for new agricultural products. These opportunities are further supported by the observation that many herbicide resistance determinants are dominant single-gene traits, rendering them amenable to gene transfer techniques (Stakker et al., 1996).

The term herbicide resistance is used to describe the ability, trait, or quality of a population of plants with a species or larger taxon, or of plant cells in culture, to withstand a particular herbicide at a dosage that is substantially greater than the dosage wild type of that plants is able to withstand, with a near normal life cycle (Dekker and Duke, 1995). Most herbicide-resistant crop cultivars were created through the stable integration of a foreign gene (transgene; transgenic plants) using recently developed techniques of molecular biology and plant transformation (Dyer et al., 1993). This approach takes advantage of the potential ability of every plant cell to be regenerated into a whole plant after receiving a foreign gene. For herbicide resistance, the gene may encode a herbicide-resistant form for an endogenous enzyme or a novel enzyme that alters and thereby inactives the herbicide. The most likely successes are considered by many to be HRCs from nonselective herbicides such as glyphosate or glufosinate or HRCs that lie in an intermediate zone between major crops such as rice, soybeans and corn and minor crops (Duke, 1996).

The development of HRCs could provide many advantages in the efficient, safe and economical production of crops (Bright, 1992; Dekker and Comstock, 1992; Dyer et al., 1993, Goldburg et al., 1990; Miller, 1991). Herbicides and their associated HRCs could be developed with less persistence in the environment (e.g., herbicide "carryover" to subsequent crops in a rotation; accumulation in other sites in the landscape, biosphere), less damage to off-site targets (e.g., adjacent susceptible crops; homes and farmsteads; surface waters), decreased undesirable movement in the environment (leaching downward through the soil profile to subsoil, ground sites; volatity and movement to off-target sites), and low acute and chronic toxicity to humans and animals.

Glyphosate

The herbicidal activity of glyphosate [(N-phosphonomethyl)glycine] and its salts was first described in 1971 (Baird et al., 1971), and since then glyphosate has become the world's most popular herbicide. Roundup is its registered trademark of Monsanto Company. The compound was identified through a conventional screening program of tertiary aminomethyl phosphonic acids (Franz, 1985). The physiological and biological characteristics of glyphosate have been reviewed (Duke, 1988) and an entire book has been devoted to this one compound (Grossbard and Atkinson, 1985). Glyphosate is a nonselective, postemergence herbicide that is used extensively prior to crop emergence, as a harvest aid, and as a directed spray. It is used extensively in forests and orchards where under story vegetation can be sprayed without contacting the foliage of the crop. It is also used in landscaping and lawns for edging and borders. It is toxicologically and environmentally benign (Duke, 1988). Upon contact with the soil, it is immobilized by binding to soil components, where is it is rapidly degraded by soil microbes, so it is extremely low toxicant to mammals, birds, and fish (Malik et al., 1989). Glyphosate is classified by the EPA (environmental protection agency) as Category E (evidence of noncarcinogenicity for humans) (57 FR 8739). Importantly, the use of the Roundup herbicide has not resulted in the occurrence of even one case of spontaneous weed resistance to glyphosate in almost 20 years of widespread use.

The primary mechanism of action of glyphosate is the inhibition of 5-enolpyruvylshikimate-3-phosphate synthase (EPSPS) (EC 2.5.1.19), the penultimate enzyme of the aromatic amino acid biosynthetic (shikimate) pathway, and plant death results from starvation for the aromatic amino acids. A resistant strain of bacteria *Salmonella typhimurium* was identified after two cycles of chemical mutagenesis and the mutation conferring resistance was shown to be in the aroA gene, which encodes EPSPS (Comai, et al., 1983). DNA sequencing revealed the presence of two independent mutations in the mutant gene: a promoter mutation conferred low levels of resistance due to elevated aroA expression, and a point mutation in the coding sequence caused a proline to serine substitution at residue 101 of the protein. Overproduction of EPSPS effectively increases the number of enzyme molecules that must be inhibited in order to block carbon flow through the pathway, and the enzyme overproduction was due to amplification of the gene(s) encoding EPSPS (Shah et al., 1986). The EPSPS with the highest tolerance to glyphosate found in the screen was CP4 EPSPS.

Glyphosate has been used extensively since its commercial introduction in 1974. The resistant gene to glyphosate has been transformed into tobacco, petunia, tomato, canola, soybean etc. (Dyer, 1994). The lead progenitor soybean line with a Roundup Ready™ (resistant gene for Roundup) gene developed by Monsanto is denoted "40-3-2". The construction and field performance of this soybean line to Roundup has been described (Padgette et al., 1989). Soybean line 40-3-2 expresses the CP4 EPSPS gene product. From this line, Roundup Ready soybeans have been commercialized rapidly.

Glufosinate (Phosphinothricin)

The herbicidal property of glufosinate [2-amino-4-(hydroxymethylphosphinyl)butanoic acid] is due to L-phosphinothricin (PPT), an analogue of glutamate. PPT is the active ingredient of the commercial herbicides, Herbiace, Basta and Liberty. Glufosinate is the most potent known inhibitor of glutamine synthetase (GS) (Devine et al., 1993). GS is critical to the assimilation of nitrogen by plants, and its inhibition leads to several immediate metabolic dysfunctions. The rapid cessation of photosynthesis brought about by glyoxylate accumulation is the important phytotoxic effect. Glyoxylate accumulates in GS-inhibited plants because the levels of amino acids required in photorespiratory glyoxylate transamination are reduced. Glufosinate is a toxicologically and environmentally benign herbicide that does not persist in the environment. Glufosinate-resistant crops have been the focus of at least two reviews (Mullner et al., 1993; Vasil, 1994). Two genes that encode enzymes that metabolically inactive glufosinate have been used to produce resistant plants by transgenic methods. The bar from *Streptomyces hygroscopicus* and/or the pat (phosphinothricine-aceytl transferase) (PAT) gene from *S. viridochromogenes* has been used to transforms about 20 crops, including wheat (Vasil et al., 1993), oilseed rape (De Block et al., 1989), rice (Rathmore et al., 1993), corn (Laursen et al., 1994), sorghum (Casas et al., 1993), barley (Wan and Lemaux, 1994), tomato (De Block et al., 1989), etc.. However, almost all of the present success in engineering PPT resistance is based on the transfer and efficient expression of the resistant bar gene in crop species (Vasil, 1996).

The bar gene was introduced into embryogenic callus or immature embryos of wheat, and the plants were regenerated on nutrient medium containing PPT. Integration of the functional gene into the plant genome was confirmed by molecular probes and resistance to topical application of Basta. Male and female transmission of the bar gene (and the resistant phenotype), which segregated as a dominant Mendelian trait, was demonstrated (Weeks et al., 1993). The bar that confers resistance to glufosinate has been transformed into rice cultivars Gulfmont, Koshihikari, Cypress, and Bengal. Field experiments on these transgenic cultivars from 1993–1995 have demonstrated that the bar gene was effective in conferring field-level resistance to glufosinate in rice (Linscombe et al., 1996). Therefore, the transgenic rice varieties that are tolerant to glufosinate (Liberty) have the potential to allow improved weed control for most of the major rice weeds, including red rice (Gravois et al., 1997; Wheeler et al., 1997). The bar gene for resistance to the herbicide is inherited as a single dominant gene, and field screening for the gene is relatively easy. Thus, traditional breeding efforts to improve the yield potential of transgenic varieties should be readily achievable (Ahrens, 1994; Gravois et al., 1997). Another novel use of resistance to PPT has been made for hybrid seed production in oilseed rape by linking it to a male sterility gene (Mariani et al., 1992).

The success of biotechnology and advantages of HRCs have made HRCs commercialized rapidly. About 15 percent of the 1997 soybean acreage was planted to herbicide-resistant soybeans from seed supplied by more than 70 companies (Rominger, 1997).

Crop Heterosis and Its Systems

The biological phenomenon in which an $F_1$ hybrid of two genetically dissimilar parents shows increased vigor at least over the mid-parent value $(P_1+P_2/2)$ is known as heterosis. The term was coined by Shull (1908) to describe the stimulation resulting from increased heterozygosity and is used synonymously with hybrid vigor which describes the beneficial effects of hybridization. Both Mendel (1865) and Darwin (1877), in their respective experiments, observed hybrid vigor in many hybrids; Darwin concluded from his observation that cross-fertilization was generally beneficial and self-fertilization injurious. Hybrid vigor was first studied systematically by Josef Gottlieb Koelreuter in the 1760's and has been recognized in many plant species during the last two centuries (Rhodes et al., 1992). Heterosis is a contraction of the phrase 'stimulus of heterozygosis' and designates the increased growth or other augmented action resulting from crossing, however it is produced. Superiority of $F_1$ hybrids over the better of their two parents is a common phenomenon in both cross- and self-pollinated crops. Such superiority may be expressed in the heterotic phenotype by increased growth, height, leaf area, dry matter accumulation, early flowering, high tolerance to stress conditions, resistance to disease and insects, and higher total yields, as well as in uniformity and agricultural homeostasis of the cultivar population. As a result, heterosis is one of the primary reasons for the success of the commercial maize industry as well as for the success of plant breeding endeavors in many other crops and horticultural plants (Stuber, 1994).

In cross-fertilized species the naturally imposed breeding system assures cross-fertilization, whereas in self-fertilized species selfing is favored by floral morphology. Hence, in cross-pollinated species problems arise particularly in the inbreeding phase providing suitable parents for the hybrid, whereas in self-pollinated species, they arise in the crossing phase of hybrid seed production. To produce hybrid seed economically, the restriction of controlled cross-pollination caused by flower morphology, especially of perfect (hermaphrodite) flowers, must be overcome. The female parent should be prevented from self- or intraline fertilization. Moreover, pollen of the male line must effectively pollinate the female line, which requires an efficient natural pollen dispersal mechanism in the male, or artificial pollination. Elimination of self- or intraline fertilization of the female line requires male sterility. Plants that fail to produce functional pollen grains are male sterile (Virmani, 1994). Such sterility can be produced by hand emasculation (castration), chemical or environmental emasculation, or manipulation of genetic male sterility or self-incompatibility.

Large-scale production of hybrid corn is done by detasselling the female parent after the disease epidemic due to Texas male sterile cytoplasm, but large-scale emasculation of species with perfect flowers (self-pollinating crops) such as wheat, rice, sorghum, tomato, etc., is practically impossible and economically unfeasible. Factors influencing the economics of hybrid production by hand or machine emasculation are ease of emasculation, number of seeds produced per flower (per pollination), number of seeds sown per unit area and the upper limit of seed prices in relation to crop production costs. Self-pollinating crops must involve use of an effective male sterility system to develop and produce $F_1$ hybrid varieties. As a result, male sterility of female parent becomes an important tool in hybrid seed production (see FIG. 1).

Three major types of male sterility are currently explored or utilized in plant breeding, i.e. cytoplasmic male sterility (CMS), environmental male sterility such as photoperiod genic male sterility (PGMS) or thermo genic male sterility (TGMS), and chemical (gametocide) induced male sterility (CIMS). Recently, transgenic male sterility system (TMSS) is actively being pursued with the success of biotechnology.

Cytoplasmic Male Sterility—Three Line System

Cytoplasmic male sterility is of special interest for hybridizing crop plants having perfect flowers with few seeds per flower and where seed prices cannot cover the cost of extra expenses involved in hand emasculation. Thus, it happened that onion was the first crop in which genetic male sterility was clearly defined and developed for production of hybrid cultivars. The crop to follow was field corn, and at present genetic male sterility serves or is useful in the production of hybrid seed of corn, rice, sorghum, pearl millet, sugar beet, alfalfa, wheat, cotton, rapeseed, onion, carrot, soybean, barley, oat, tomato, sunflower, petunia, tobacco, pepper etc. (Frankel and Galum, 1977). Since 1976, when hybrid rice was first cultivated commercially, its area has increased to 17 million hectares (ha) by using CMS system (Table 1). Over the years, this technology has helped the country to produce 200 million tons (t) more paddy rice; thus establishing its strategic significance in increasing national food production (Yuan et al., 1992). With an average yield of 6–7 t/ha from 17 million ha in China (Table 2), hybrid rice contributes about 20% of the world's total rice production. CMS was the major system in hybrid corn before the destructive leaf blight epidemics associated with Texas male sterile cytoplasm (T-cms) occurred in the late 1970's.

The CMS system is controlled by the interaction of cytoplasmic and nuclear genes. Presence of homozygous recessive nuclear gene(s) for fertility restoration in association with sterility including genetic factor(s) in cytoplasm make a plant male sterile (A line). In the absence of a sterility-inducing genetic factor(s) in the cytoplasm, plants become male fertile. In such a cytoplasm, if fertility restorer nuclear gene(s) are recessive, the plants will maintain sterility of the male sterile plants and such plants are designated as maintainers (B line). If fertility restorer nuclear gene(s) present in an individual with or without sterility-inducing cytoplasm are dominant, the plant will restore fertility in a hybrid derived by crossing it with a CMS plant or A line and such a plant is designated as restorer (R line). Therefore, CMS system is called three line system, i.e.

a. Male sterile (MS) line, called A line: Male sterility is required over 99.0% in rice and its female organs are completely normal (Table 3).
b. Maintainer line, called B line: B line maintains male sterility for A line i.e. the offsprings of A and B line have male sterility above 99.0% in rice for the multiplication of A line.
c. Restorer line, called R line: R line restores male fertility of the hybrids i.e. the offsprings of A and R line have seed set above 80% in rice.

There are two cycles for hybrid seed production in this system (see FIG. 2):

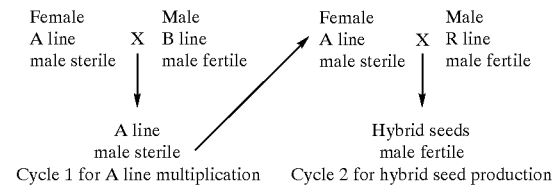

The conversion of male sterility and fertility is controlled by its genetic interaction between cytoplasm and nucleus. This male sterility is relatively stable regardless of location, time, weather etc. In addition to breeding agronomically, genetic match for male fertility alternation among A, B and R lines is very strict and essential. That is A line must contain complete male sterile gene in both its cytoplasm and nucleus. Male fertile gene must be in the cytoplasm of B line only. Male restoring gene must be in the nucleus of R line that has to bring fertility of its hybrid back to normal. The stability of male sterility is the major reason for this system to stay on the stage by itself (Yuan and Fu, 1995).

The two cycles for hybrid seed production in the CMS system make the procedure not only complicated and costly, but also easy to be contaminated in the final product, hybrid seed. In any step of the cycles, the parents involved have a chance to be contaminated or mutated, and the contaminations or mutants accumulate in the final product, hybrid seeds. Here we take rice as an example since it is the most successful crop in self-pollinated crops for heterosis utilization. If one panicle from B line is mixed and harvested with A line in the first cycle, 80–100 plants of B line are mixed in the population of A line in the second cycle. Each plant generates 10 panicles and 80–100 spikelets on each panicle so that 800–1000 B line seeds from one seed of 1st cycle are mixed with hybrid seeds. In addition, each spikelet from 80–100 B line spikelets per seed of 1st cycle contains 6 anthers, each anther contains thousands of pollen, and after these anthers pollinate to A line plants around, tens of thousand of A line individuals are expected. Totally, 8–10 million impure plants from the single panicle are expected in each hybrid rice field. If R line has some offtype plants, the number of impure plants in the hybrid rice field would be more.

In a hybrid rice field, some impure plants have different height of plant from the true hybrid, some flower at different times so that early heading plants lodge or shatter when harvesting, and late heading plants do not mature or do not flower when harvesting, and some are male sterile without seed set at all. Obviously, these impure plants result in a great yield loss. Research showed that every one percent decrease in the purity of hybrid seeds would cause a yield loss of 80–100 kg per hectare (Yuan and Fu, 1995). Hybrid rice was cultivated in over 17 million of hectares in 1991 (54.1% of total rice cultivation), so a great amount of rice was possibly lost due to a lack of hybrid purity.

The Chinese government sets the standards of hybrid seed purity above 96% and impure plants less than 0.2% in a hybrid rice field (Table 3). If seed quality data for a seed lot does not meet these standards, the whole lot of hybrid seed (50,000–100,000 kg) can not be used for seeds, and must be used instead for animal food because the grain quality of hybrid seed is not marketable. If a particular field has impure plants above the national standard, a legal argument between the seed company and farmer occurs. In order to meet the criteria of hybrid seed, the seed company has to take time consuming and expensive steps to (Lou and Mao, 1994):

A. Purify the A, B and R lines, respectively, and crossing among them to check the genetic match for foundation seed production.

B. Be very cautious in operations in hybrid seed production including:
  1. Isolation such as distance, flowering time and objects (belt of trees, bamboos, mountain etc.)
  2. Rogueing from time to time, especially during heading period.
  3. Harvesting, threshing and drying on the ground separately from any others.

C. Purity identification. When the hybrid seed is harvested in late August or early September, a standard sample covering a seed lot is immediately taken and planted in Hai-nan Island (natural winter nursery). A sample has to contain more than 1000 plants for scoring impure hybrids. For instance, Sichuan province (one of 30 provinces in China) has more than 3 million hectares of hybrid rice annually. Each hectare needs at least 15 kg of hybrid seed and 45–50 million kg of seed is demanded, so 5000 samples have to be identified.

Furthermore, the quality data is not collected until March of the next year when hybrids head i.e. a month from planting season in Sichuan. However, the seed company has to get the seed contracted at the end of the year and distributed at beginning of the next year. As a result, no quality data is available when seed is distributed which leads to legal arguments later on.

In this rice example, the great investment of resources raises the seed cost and the lack of purity data when the seed is distributed creates an unsure production and legal problems.

Moreover, male sterile cytoplasm is not easily found to meet the CMS breeding requirements and the genetic match among the three lines (A line, B line and R line), which was one of the major cause of the disease epidemics in the U.S. maize industry in 1970's. The Texas (T) male sterile cytoplasm (cms-T) of maize was discovered in 1944 in the Golden June Line. Although other CMS occur in maize (e.g., cms-C and cms-S), cms-T proved to be superior for hybrid seed production because most inbred lines are completely and stably sterilized in Texas cytoplasm, and fertility restoration is more easily achieved. $Rf_1$ and $Rf_2$, two dominant nuclear alleles, act jointly to suppress CMS in cms-T maize. The $Rf_2$ allele is present in most widely used inbred lines, whereas the $Rf_1$ allele is rare. In the two decades before the U.S. epidemic of Southern corn leaf blight of 1969 and 1970, the conversion of inbred parents to cms-T replaced detasseling as the predominant form of pollen control. By 1970, 85% of the hybrid maize grown in the United States carried this cytoplasm. The combination of a physiological specialized race of a pathogen, favorable weather, and cytoplasmic uniformity made the Southern corn leaf blight of 1970 one of the more damaging and widely dispersed epidemics in the history of plant pathology. In excess of 15% of the U.S. maize crop was destroyed (Ullstrup, 1972). After it was determined that cms-T is specifically susceptible to *Bipolaris maydis* race T, large-scale use of cms-T by the hybrid seed corn industry was immediately abandoned (Williams and Levings, 1992).

Male sterile cytoplasm uniformity occurs also in hybrid rice production in China. Although many male sterile cytoplasms have been discovered, very few of them can be used to develop desired CMS lines that are released commercially. In 1994, about 90% of the CMS lines used in commercial production contained W type male sterile cytoplasm which was from a male sterile wild rice plant (Mao, C. X., 1994). Thus, about 90% of the rice fields out of 17 million hectares are covered by W type CMS inspite of the destructive lesson in maize.

Furthermore, the complexity involving three lines and their genetic interactions limits the utilization of heterosis. For example, high yield and quality are rarely achieved together in the hybrids of rice. Also, CMS works only in low ploidy crops such as diploid rice and corn, but not in high ploidy crops i.e. hexploid wheat.

Environmental Genetic Male Sterility (EGMS)—
Two Line System (see FIG. 3)

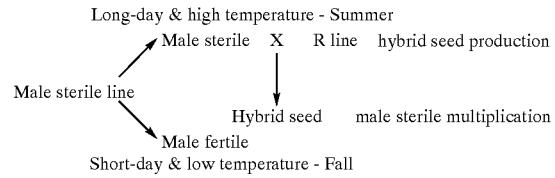

Photosensitive genic male sterility (PGMS) and thermosensitive genic male sterility (TGMS) are involved in this EGMS system. The male sterility of PGMS and TGMS is controlled by nuclear genes and has no relationship to the cytoplasm. Under long-day length or high temperature condition (Summer), the plants show male sterile, and under short-day length or low temperature (Fall), they become male fertile. Therefore, this system has two advantages over the CMS three-line system. Firstly, female parent line can be used as dual purposes i.e. hybrid seed production in Summer and self-multiplication in Fall (no need for a maintainer), which simplifies hybrid seed production. Secondly, it is more efficient to obtain superior hybrids because nearly all normal varieties have restoring ability to the male sterility regardless of restoring genes (no need for a specific restorer), which increases the range of male parent selection for breeding objectives. The former decreases seed cost and the latter increases breeding efficiency. It was reported that remarkable progress of EGMS has been made in rice, wheat, corn, sorghum, oilseed rape, cotton, etc. in the International Symposium on Two-line System Heterosis Breeding in Crops in China in 1997.

However, seed purity has kept this elite system in experimental stage since 1981. In japonica rice, there are PGMS, TGMS and P-TGMS (photo-thermosensitive genetic male sterility). Among indica environmentally induced genetic male sterile lines, no PGMS lines were found and most of them were TGMS and P-TGMS (Cheng et al., 1996). In nature, variation of day length is almost regular and heading time can be arranged through planting time, but variation of temperature is not precisely regular. Therefore, PGMS line can be operated for dual purposes in the production instead of TGMS and P-TGMS. Heterosis is not so pronounced in japonica. Indica rice is the major rice in China as well as in Asia. Missing of PGMS in indica is the major reason for the EGMS two-line system not to function commercially. Research data indicated that temperature above 24° C. is a strict requirement for the male sterile line to express male sterility completely in addition to long-day photoperiod (Yuan and Fu, 1995). For example, Hunan (province) seed company had 600–700 hectares of hybrid seed production using Pei-ai 64 as male sterile line in 1996. Unfortunately, a rain along with temperature drop during heading period made some male sterile plants or panicles become fertile or partially fertile (Zhu, Xudong, personal conmm.). Again, this system has failed to get on the commercial stage.

Chemically-Induced Male Sterility (CIMS)

Male sterility in crop plants is also induced physiologically by chemicals known as male gametocides, pollen suppressants and chemical emasculators and their female organs function normally in order to receive pollen from male parent for hybrid seed production (see FIG. 4). This system is even simpler or more efficient than the EGMS two-line system. It does not require any special scheme for the development of male sterile and restorer parents, and the maintenance and increase of parental seeds are simple (Virmani, 1985). No need of breeding female parent or any special breeding program of the CIMS system further reduces seed cost of hybrid and no limitations for parent selection increases the breeding efficiency further. The less aspects a breeder requires, the greater chance he gets the hybrid. Research has been conducted since late 1960's, and male killer 1 (Saxungji 1 hao), male killer 2 (Saxungji 2 hao) etc. have been named for induction chemical in China.

An ideal male gametocide should: (1) selectively induce pollen sterility without affecting female fertility, (2) be systematic or sufficiently persistent to sterilize both early and late flowers on the same plant, (3) should have no mutagenic effect, (4) have reasonably broad "window" or target period of application to overcome the effects of adverse weather conditions and variable crop growth, and to permit treatment of large hectarages, and (5) have no undue hazard either to man or plant (Virmani, 1994).

However, to-date, no gametocides meet all these strict requirements so that chemical emasculation has been unreliable on a commercial scale. Many mutagenesis with such compounds as streptomycin sulfate, mitomycin C, ethidium bromide (Jan and Rutger, 1988), and others as napthalene acetic acid (NAA), RH 531 [sodium-1(p-chlorophenyl)-1, 2-dihydro-4, 6-dimethyl-2, oxonicotinate], maleic hydrazide, gibberellins, FW 450 (sodium alpha beta-dichlorosisobutyrate), ethrel (2-chloroethyl phosphonic acid) and methyl arsenate salts (zinc methyl arsenate, sodium methyl arsenate), etc. (Virmani, 1985) have been proved to induce male sterility, and research has been conducted in wheat, rice, rapeseed, corn, etc. for decades. The major barrier for CIMS success is the difficulty in achieving high percentages of pure hybrid seeds economically.

The effectiveness of male sterile induction depends on:
a) Rate of the chemical—low rate does not guarantee complete male sterility, but high rate results in other physiological disorders such as partial exsertion of panicle out of the leaf sheath, irregularly flowering or no flowering for some spikelets, incomplete panicle development or even some injuries to stigma, the female organ, etc. In return, these disorders reduce hybrid seed production, and increase seed cost.
b) Development stage of panicles—cereal crops have unlimited tillering ability, which bring about the panicles at different developing stage in a plant, so that the sensitivity to the chemical is different among panicles.
c) Environmental conditions of application—for example, temperature has to be in a small range for a period and without rain interfering with the application, etc.

Transgenic Male Sterile System (TMSS)

Mariani et al. (1990) reported a new genetic male sterility system developed by means of genetic enginnering in tobacco and oilseed rape (Brassica napus). The system invloves the use of a tapetum specific gene, TA29 isolated and cloned from the tobacco genomic library. The chimaeric ribonuclease (RNase) T1 and barnase genes containing the tobacco TA29 gene promoter can induce male sterility. The TA29 gene is highly regulated and transcribed specifically in tapetal cells that surround the pollen sacs in the anther. Expression of the cytotoxic TA29-RNase genes selectively destroys the tapetal cell layer, prevents pollen formation, and results in male sterility (Mariani et al., 1990). The TA29-barnase gene contains the coding sequence for the extracellular RNase which has a corresponding inhibitor protein, called barstar. Barstar is produced intracellularly and protects the bacteria from the lethal effects of barnase by forming a stable complex with barnase in the cytoplasm, and acts as a dominant restoring gene for male fertility in plants. The TA29-barnase gene also acts as a dominant male sterility gene (Mariani et al., 1992), so the multiplication of the transgenic male sterility female plants has to be dependent on crossing with the wild type plants. Therefore, the male sterility inducing gene is linked to a selectable marker gene i.e. bar that confers resistance to the herbicide i.e. glufosinate for producing a 100% sterile female plants. Then, the offsprings from the cross segregates 50% male-sterile, glufosinate-resistant plants, and 50% male-fertile, glufosinate-susceptible plants (Denis et al., 1993). The 50% male-fertile, glufosinate-susceptible plants are cleaned up by spraying glufosinate on the female population in hybrid seed production. Pioneer Hi-Bred Intl. reported an improved way of this cleaning in hybrid corn program: seed coating, i.e. the seeds for producing female plants are coated with herbicide glufosinate, which makes the 50% fertile plants not germinate or die during the germination in the field (Songstad et al., 1997).

Hence, there is a need for an improved crop, plant, or seed heterosis or hybridization system, process, or the like.

BRIEF SUMMARY OF THE INVENTION

In accordance with the present invention, an improved process for the efficient production of hybrid plants, crops, or seeds is provided. More particularly, the present invention is directed to crop or plant heterosis or hybridization, wherein the female parent is male sterile and the male parent is preferably male fertile and has a herbicide resistant gene or genes which is passed on to the pure hybrid seeds, plants, or crops. The hybrid seeds, plants or crops produced by the present process are treated or sprayed with the herbicide or herbicides and all seeds or plants that are not pure hybrids from a crossing with the herbicide resistant transgenic male parent and weeds are killed. The remaining live crop, plant, or the like is the true pure hybrid.

In accordance with the present invention, provision is made for an improved seed, crop or plant heterosis or hybridization process or system including an improved CMS system, EGMS system, CIMS system, and improved basic heterosis, wherein the male parent is male fertile and includes a herbicide resistant gene or genes which is passed on to the hybrid seeds.

The present invention also finds special applicability to the production of hybrid seeds, wherein hybrid purity can be identified for a particular seed lot prior to planting of the hybrid seeds.

Heterosis designates the increased growth or other augmented action resulting from crossing, however it is produced. Male sterility of female parent is an important biological mechanism for the commercial production of hybrid seed. Male sterility can be created by genetic manipulation, environmental influences, chemical induction and biological engineering. In principle, male sterility is a physiological disorder and the creation of complete male sterility either is costly or brings about other physiological disorders. Integrating the resistance gene to a non-selective herbicide into male parent and spraying the herbicide onto the hybrid population resulting from mating with the male parent for securing hybrid purity reduce the strict demand for complete male sterility. Therefore, simple and practical methodologies such as environmental and chemical means can be employed in the induction of male sterility, and the conflict of male sterility with other physiological disorders can be well balanced. The concept of this invention is applicable to all the crops and plants in which male sterility has been studied for heterosis purposes including rice (*Oryza sativa* L.), wheat (*Triticum aestivum* L.), corn (*Zea mays* L.), cotton (*Gossypium hirsutum* L.), soybean (*Glycine max* L.), sorghum [*Sorghum bicolor*(L.) Moench], rapeseed (*Brassica napus* L.), barley (*Hordeum vulgare* L.), oat (*Avena sativa* L.), rye (*Secale cereale* L.), pearl millet [*Pennisetum typhoides* (Burm) Stspf et Hubb.], alfalfa (*Medicago sativa* L.), tomato (*Lycopersicon esculentum* L.), sugar beet (*Beta vulgaris* L.), sunflower (*Helianthus annuus* L.), onion (*Allium cepa* L.), petunia (*Petunia hybrida* Hort.), and carrot (*Daucus carota* L.).

The application of non-selective herbicide with its resistant gene in hybrid seed production for utilization of heterosis includes:

a) integrating the herbicide resistant gene into the male parent;

b) pollinating male sterile female parent, however the male sterility comes from, with the transgenic male parent; and, c) spraying the hybrid population with the matched herbicide for hybrid purity control and weed control in the production.

The above-described protocol could be used in the following crops and plants in which research of male sterility for heterosis utilization had been conducted. They are rice (*Oryza sativa* L.), wheat (*Triticum aestivum* L.), corn (*Zea mays* L.), cotton (*Gossypium hirsutum* L.), soybean (*Glycine max* L.), sorghum [*Sorghum bicolor*(L.) Moench], rapeseed (*Brassica napus* L.), barley (*Hordeum vulgare* L.), oat (*Avena sativa* L.), rye (*Secale cereale* L.), pearl millet [*Pennisetum typhoides* (Burm) Stspf et Hubb.], alfalfa (*Medicago sativa* L.), tomato (*Lycopersicon esculentum* L.), sugar beet (*Beta vulgaris* L.), sunflower (*Helianthus annuus* L.), onion (*Allium cepa* L.), petunia (*Petunia hybrida* Hort.), and carrot (*Daucus carota* L.).

A principal object of the present invention is the provision of an improved, simplified, economical heterosis or hybridization process and an improved hybrid product, seeds, plants, crops, and the like having high hybrid purity, high yield, hybrid vigor, and the like.

A still further object of the present invention is the provision of an improved heterosis process including the use of a male parent which is male fertile and includes a herbicide resistant gene which is passed on to the hybrid seeds, plants, and crops.

A still further object of the present invention is the provision of an improved CMS system, EGMS system, CIMS system, and the like utilizing a male parent which is male fertile and has a herbicide resistant gene.

A still further object of the present invention is the provision of a new and improved hybridization process for producing and improving the production of high hybrid purity seeds, crops, plants, and the like more efficiently, economically, with higher yields, and with higher hybrid purity.

Other objects and further scope of the applicability of the present invention will become apparent from the detailed description to follow, taken in conjunction with the accompanying drawings, wherein like parts are designated by like reference numerals or characters.

DETAILED DESCRIPTION OF THE INVENTION

Figure 1:
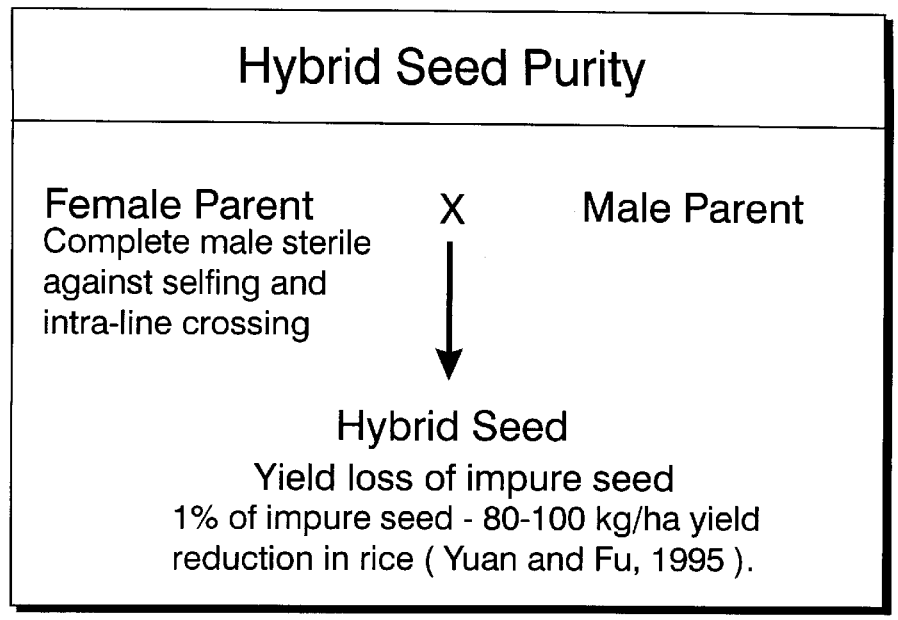
FIG. 1 is a schematic representation of heterosis or hybridization.
Figure 2:
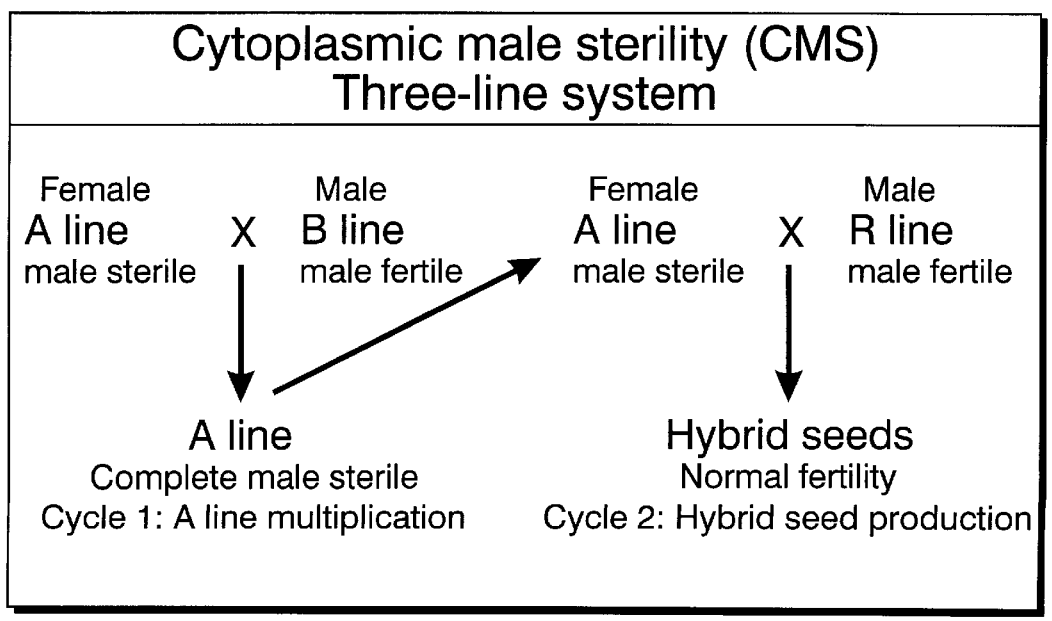
FIG. 2 is a schematic representation of cytoplasmic male sterility heterosis system or process.
Figure 3:
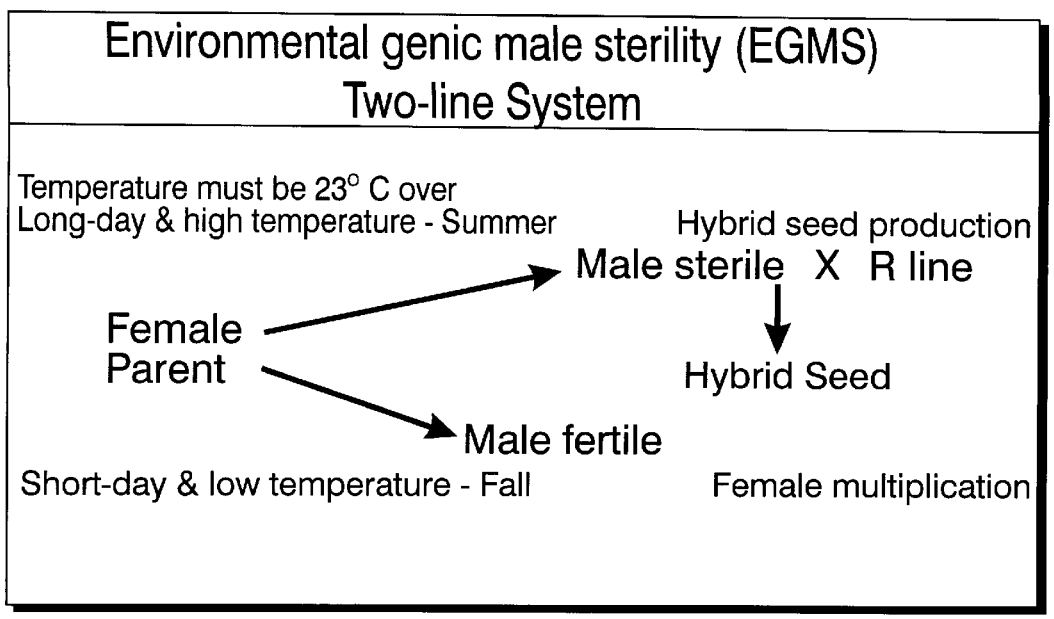
FIG. 3 is a schematic representation of environmental genic male sterility heterosis system or process.
Figure 4:
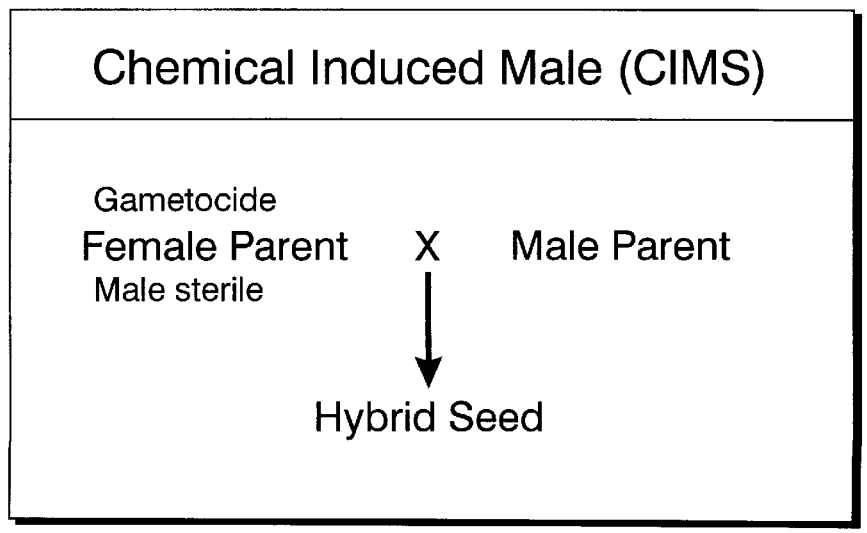
FIG. 4 is a schematic representation of chemical male sterility heterosis system or process.

In accordance with the present invention, there is provided an improved process for the efficient production of hybrid seeds with a security of hybrid purity in the field production for all crops and plants capable of allowing incomplete male sterility for female plants, which increases genetic diversity of the CMS system (many male sterile lines that are not male sterile absolutely can be used), which simplifies the procedure of hybrid seed production (using environmental genetic male sterility or chemically induced male sterility instead of cytoplasmic male sterility), and which utilizes heterosis more effectively and economically.

In accordance with one embodiment of the present invention, a crop, plant or seed heterosis or hybridization process includes the steps of:

1) Integrating a resistant gene to a type of non-selective herbicide, i.e. Liberty (glufosinate) or Roundup (glyphosate) into a cultivar of any crops or plants which will be used as male parent in a heterosis process, system or program by gene transformation, bombardment, or any other genetic molecular technology, protocol or hybridization, and multiplying this transgenic or hybridizing male parent as many times as necessary for seed demand.

2) Pollinating a male sterile female population (no matter how the male sterility of female parent is produced) with the transgenic or hybridizing male parent, and harvesting hybrid seeds from the female plant population.

3) Planting the hybrid seeds for hybrid plants or crops and spraying the hybrid seedlings with the herbicide matched to the integrated resistant gene i.e. Liberty or Roundup, to kill all the false hybrid plants from either selfing of female parent due to contamination, incomplete male sterile conversion because of genetic reasons in CMS system, environmental influences i.e. temperature in EGMS system, and any other reasons from male sterile induction (chemical, or physical factors), or hybridizing with offtype plants and incomplete male sterile plants in male sterile female parent population, and off-type plants in the male parent population. All false hybrid plants are eliminated because all these false hybrid plants do not have the resistant gene to the herbicide, conversely, all the true hybrid plants do not suffer from the herbicide because they have the resistant gene transferred from the true transgenic or hybridizing male parent through pollination and because the resistant gene to the herbicide is inherited as a simple dominant allele (Ahrens, 1994; Gravois et al., 1997). This process may be more economical if a nursery is employed for the crop or plant such as rice in Asia, tomato etc. because less area is needed to spray for hybrid purity control. Although more herbicide is sprayed directly on the production field for most crops or plants, control for both any false plants in the hybrid population and any weeds in the field is achieved at same time.

4) Spraying the field with the selected herbicide any time during the season for weed control as necessary.

Figure 5:
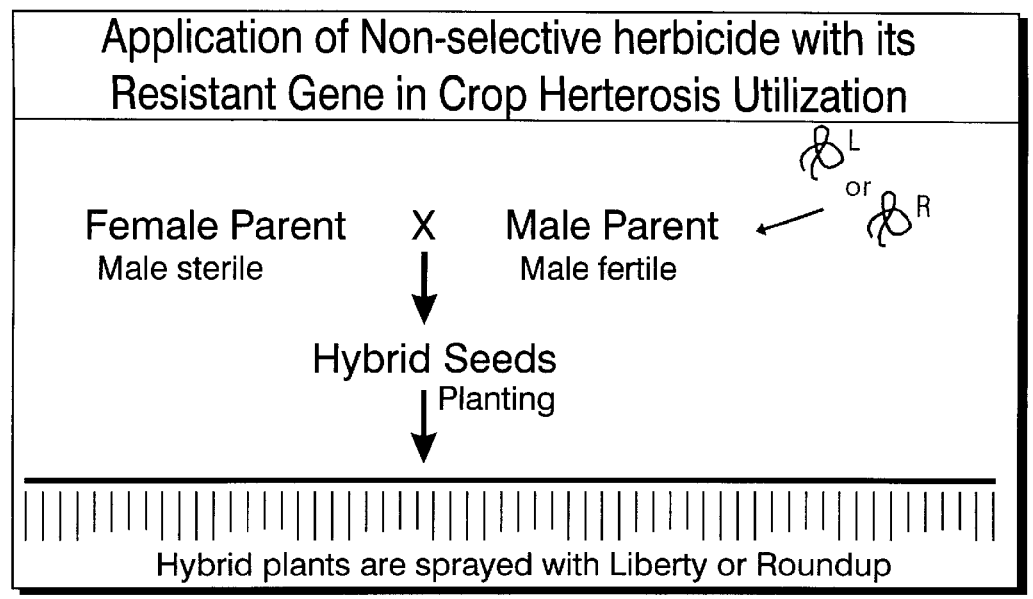
FIG. 5 is a schematic representation of the improved seed, plant or crop heterosis process of the present invention.
Figure 6:
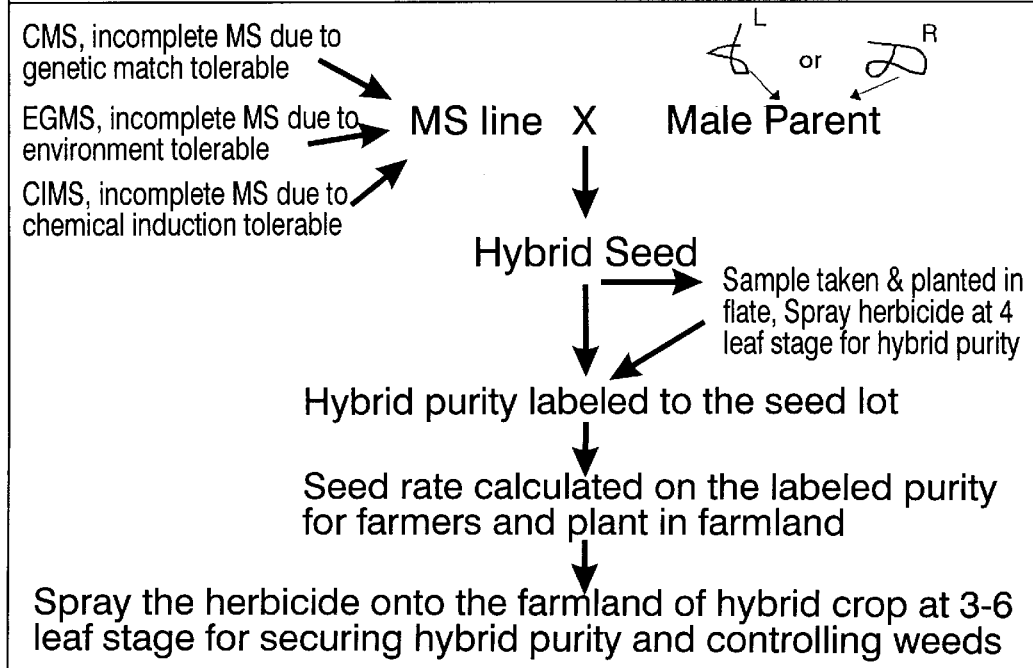
FIG. 6 is a schematic representation of the improved CMS, EGMS, and CIMS heterosis system or process of the present invention.

With reference to FIGS. 5 and 6 of the drawings, the conventional heterosis or hybridization systems or processes of FIGS. 1–4 of the drawings are improved upon and simplified by utilizing a male parent which is not only male fertile, but also contains a herbicide resistant gene for a selected herbicide or herbicides. As shown in FIGS. 5 and 6, the present invention is equally applicable to not only basic crop or plant heterosis, but also CMS, EGMS, CIMS, and combinations thereof.

Also in accordance with the present invention, the female parent male sterility (MS) line need not have complete or pure male sterility and in so doing provides for a much broader spectrum of MS line plants, crops, and the like which are less costly to produce due to their lack of purity, or tolerant to climatic or environmental changes or conditions, and allows for a broader spectrum for plants or crops to use as MS line which could not be used in conventional CMS, EGMS, or CIMS systems, and further allows the MS line to have enhanced or improved characteristics or features because of the reduced requirement for 100 percent sterility or purity in the MS line.

Also, as shown in FIG. 6 of the drawings, the present invention provides for a seed production system or process, wherein the hybrid purity of the seed lot can be identified and labeled prior to planting. This allows for a more accurate prediction of the worth or price of the seed lot and also reduces legal and production risks.

Still further, the present invention provides that an initial and subsequent sprayings of the crop or plants in the field or in a nursery with a herbicide to which the pure hybrid seeds and hybrid plants are resistant serves to not only kill impure hybrids, but also weeds and the like. Further, with respect to certain crops which in the past require directed spray of selected herbicides, for example, non-herbicide resistant corn, cotton, and the like, the crop or plant heterosis or process of the present invention provides for and allows for non-directed or generalized spraying of the plants or crops with this selected herbicide or herbicides to which the plants are resistant. This may also reduce cost, increase in efficiency, and increase yield.

A. Experimental Evidence

Figure 7:
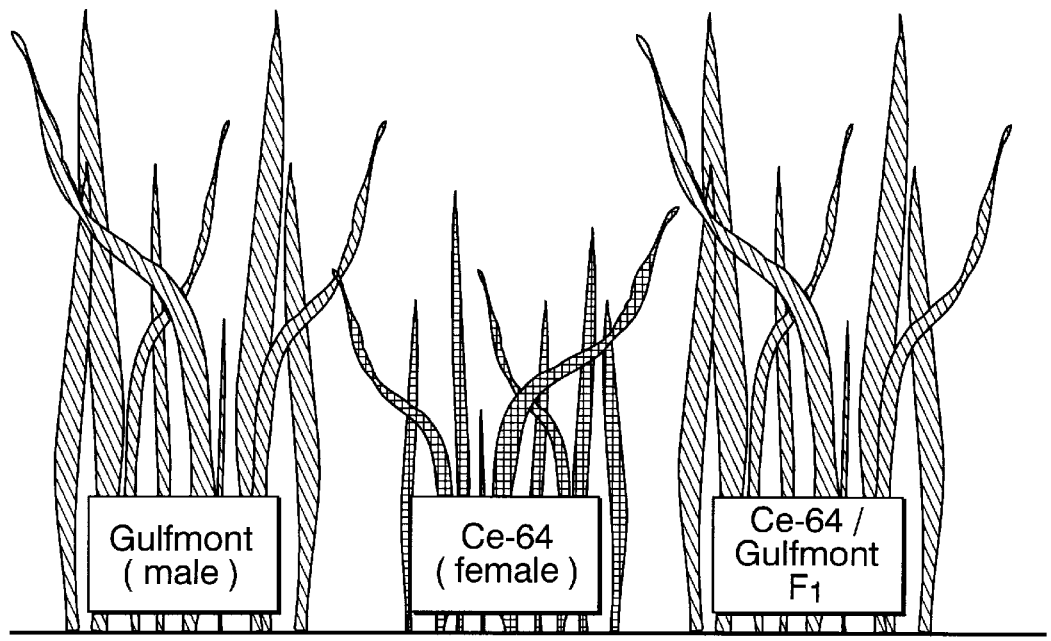
FIG. 7 is a photographic representation of the results of a demonstration that a dominant gene to Liberty resistance was transferred to $F_1$ hybrid through pollination from transgenic male parent in accordance with the present invention.
Figure 8:
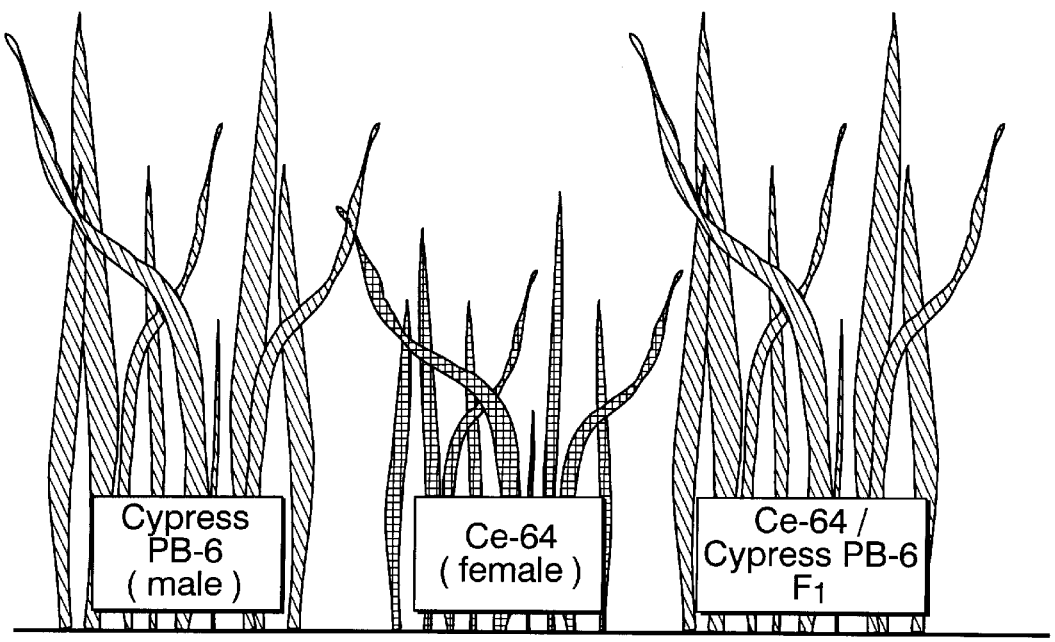
FIG. 8 is a photographic representation of the results of a demonstration that a dominant gene to Liberty resistance was transferred to $F_1$ hybrid through pollination from transgenic male parent in accordance with another embodiment of the present invention.

One or more experiments have been conducted to verify the effectiveness of the present invention. Ce-64, one of the popular parent in commercial hybrid rice, was emasculated mannually, and pollinated mannually with Liberty Link transgenic rice varieties, Cypress PB-6 and Gulfmont, respectively. Hybrid seeds were harvested from the female parent, Ce-64 and then, planted in a plastic flat (20×16×3 inches). The hybrid seedlings in the flats were sprayed with Liberty (glufosinate) at the rate of 1.0 lb a.i.(active ingredient) per acre one month after seeding. The following data were recorded on the 9th day of the herbicide treatment. In the cross of Ce-64 X Gulfmont (transgenic), 70 plants of female parent Ce-64 died completely, conversely, 58 plants of male parent Gulfmont and 35 plants of $F_1$ hybrid were alive (FIG. 7). In the cross of Ce-64 X Cypress PB-6 (transgenic), 63 plants of female parent Ce-64 were dead completely, however, 83 plants of male parent Cypress PB-6 and 46 plants of $F_1$ hybrid were alive and grew normally (FIG. 8). This experiment demonstrated the feasibility of the invention: the dominant Liberty Link gene was transfered to $F_1$ hybrid plants through pollination. Therefore, any plants that are not from the pollination of transgenic male parent in the $F_1$ hybrid population (including the female parent or mother plants) are eliminated by the herbicide.

Application Areas

1). Multiplication of male parent: The non-selective herbicide is sprayed on the multiplication field of male parent which is transformed with the resistant gene to the herbicide. All the contaminated plants including rice and weeds in the male parent population are eliminated.

2) Improved Three-line system: The resistant gene is integrated into the male parent that is used for hybrid seed production. All the impure rice plants from either selfing of contaminated individuals in male sterile line (female) population, or hybridizing with intra-lines or plants in female parent and with offtype plants in male parent population are eliminated by spraying the herbicide on the field of hybrid seedlings. The remaining plants are pure hybrids from hybridizing with the transgenic male parent.

The Chinese government requires 100% of male sterility for female parent because of serious yield reduction from low hybrid seed purity. For grain crops such as wheat, rice, corn, canola, etc., the harvest part or economical part—grain is from fertilization, which requires $F_1$ hybrid plants with normal fertility for achieving the heterosis economically. As a result, economical 100% male sterility for female parent and normal fertility for hybrid plants are two keys in crop hybrid systems.

However, 100% male sterility of female parent and normal fertility of hybrid plants from the male sterile female parent are two extreme points of a conflict. In cytoplasmic male sterile hybrid system, male sterility of female parent is decided by the genetic conflict or genetic distance between cytoplasm and nucleus of the hybrid female parent. Usually, the larger the genetic distance causing the genetic conflict between cytoplasm and nucleus is, the greater the male sterility will be. For example, W-Zhenshan 97A, a male sterile female parent covering over 80% of 17 million hectares of hybrid rice in China currently, contains a cytoplasm from the male sterile wild rice and a nucleus from an early indica native variety, Zhenshan 97. The female parent for G-type hybrid rice which is popular in southwest China contains a cytoplasm from an indica variety, Gambiaka Kokoum from Guyana, West Africa. The fertility of hybrids is decided by the genetic interaction between the male sterile female parent and male parent or restoring line. Actually, the genetic interaction is the interaction of three genetic backgrounds i.e. cytoplasmic donor, nucleus donor and restorer donor. Usually, the greater the male sterility of female parent resulting from a larger genetic distance between its cytoplasm and nucleus is, the harder it is to restore the fertility of its $F_1$ hybrid plants by the restoring line. In practice, a successful hybrid system requires 100% male sterility of female parent and normal fertility of $F_1$ hybrids for enough heterosis on grain yield. That is the combination system of the most conflict between cytoplasm and nucleus in the female parent and the most restoring ability from male parent. This combination is a perfect genetic match among the three donors. Breeding practice has proved that such a serious genetic match is so limited in nature that uniformity on a large scale is unavoidable. The uniformity generates genetic vulnerability that is responsible for destructive epidemics. For instance, Texas male sterile cytoplasm (cms-T) covered over 80% of hybrid corn acreage in the U.S. when destructive leaf blight epidemics occurred in the late 1970's. Currently in 17 million hectares of hybrid rice in China, W-type male sterile cytoplasm and maintainer, Zhenshan 97, the nucleus donor have being covered over 85% of hybrid rice since their release in the 1970's, and the restorer, Minghui 63, has been planted in over 85% of hybrid rice area for over 15 years even with full knowledge of the corn disease epidemics (Mao, 1994).

The major reason for such great uniformity is the shortage of substitute varieties to fit in this genetic match of the breeding program. However, if one of the two extreme points is losing a little i.e. allowing partial fertility for male sterile line that is the result from decreased genetic distance between cytoplasm and nucleus, the fertility restoring of hybrid will be easier because the conflict of sterility and fertility will be decreased. Then chance for breeding other substitutes for each member of the system will be enlarged. As a result, the uniformity will be broken down and the genetic diversity will be increased. For example in China, male sterile line II-32A, You-1A, Ke-zhenA etc. have greater outcrossing yield that results in lower hybrid seed cost, and larger range of mating with male parent that results in higher chance of heterosis because they do not require as strong restoring ability as restorer Minghui 63 when compared to current hybrids. But these male sterile lines have only 95% male sterility, or even lower when environmental conditions change, so they cannot be released for commercial use due to crop production stability requirements (Yuanching Li, personal comm.).

The present invention addresses crop production stability requirements while allowing for a reduction in the conflict between male sterility and fertility. Even though a male sterile line has 5–10% or even higher male fertility, all the seeds from its selfing or intraline pollination will not contain the herbicide resistant gene such as Roundup Ready or Liberty Link because their pollen do not come from the transgenic male parent. Only those seeds set in male sterile plants or spikelets in the population are true hybrids crossed with the transgenic male parent because only male sterile plants or spikelets have chance to receive foreign pollen. And only the true hybrid plants in the field can survive alone from the herbicide sprayed to the field. Therefore, allowing the male sterile line not to be completely or 100% male sterile and eliminating all contaminating or false hybrid plants in the field by spraying the herbicide are two of the major points of this invention and also two of the major advantages of this invention. These advantages balance the two extreme points, eliminate the genetic match of three donor, and create more opportunities for breeding program so that the genetic diversity is or can be increased and the heterosis will be enhanced in crop production.

Also, the time-consuming and serious identification procedure for hybrid seed purity is eliminated. Any risks in yield loss due to hybrid purity in rice production that always become legal arguments between the seed company and the farmers are avoided.

All these advantages will make the cost of hybrid seed greatly reduced and greater cultivation acreage of hybrid crop will be expected throughout the world.

3). Improved Two-line system (FIG. 6): The resistant gene is inserted into the male parent and the transgenic male parent pollinates either TGMS or PGMS or P-TGMS. When spraying the herbicide on the field of hybrid seedlings, the plants from either selfing of contaminated individuals in male sterile line (female) population and fertile plants or panicles of male sterile plants due to enrivonmental variation i.e. temperature, or hybridizing with intra-lines or plants in female parent and with offtype plants in male parent population are eliminated by spraying the herbicide on the field of hybrid seedlings. The remaining plants are pure hybrids from hybridizing with the transgenic male parent. As a result, a few fertile individuals in male sterile population due to unexpected environmental variation such as temperature drop is tolerable because they will be killed with herbicide. Hence, this system can be used commercially. The elimination of the maintainer line saves about half of resources invested in conventional hybrid seed production. Also, the elimination of the restoring ability requirement for the male parent increases the range of male parent selection to mate with female parent so that there is greater opportunity for breeding higher yield and better quality i.e. greater heterosis is generated. This invention helps a two-line system to replace the conventional three-line system because of the two eliminations in addition to lower seed cost.

4). Improved chemically induced male sterile system (FIG. 6): The resistant gene is inserted into the male parent and the transgenic male parent pollinates male sterile female parent induced by chemical. By spraying the herbicide on the field of hybrid seedlings, the plants from either selfing of fertile plants or panicles of the female plants due to incomplete male sterile induction by chemical and contaminated individuals in the female population, or hybridizing with intra-lines or plants in female parent and with offtype plants in male parent population and weeds are eliminated. The remaining plants are pure hybrids from hybridizing with the transgenic male parent. As a result, a few fertile plants or panicles in male sterile population due to incomplete chemical induction are tolerable, which reduces the conflicts between induced male sterility and other physiological disorders by using a lesser amount of the chemicals and provides the feasibility for this system to be used commercially. In this improved system, the main consideration is heterosis on any aspects such as yield, quality etc. either individually or together. Therefore, this system makes the best better. This improved CIMS system may play a major role in crop hybrid production.

5). Case illustrations of application in wheat, rice, corn and canola Wheat (*Triticum aestivum* L.)

Wheat is the largest crop cultivated and produced in the world. Annual wheat cultivation is about 223 million hectares in the world and 25 million hectares in the U.S. Annual production of wheat is about 560 million metric tons in the world and 65 million metric tons in the U.S.

For this major crop, heterosis utilization is always a hot topic world wide. Currently, some private companies are trying to utilize wheat heterosis by the aid of chemically induced male sterility (CIMS) or gametocide because cytoplasmic male sterility has proven to be hopeless. For example, HybriTech Seed International (HTSI), a unit of Monsanto company, is promoting 'Quantum' system including a series of wheat hybrids that are produced through CIMS (HybriTech, 1997). WAVES, a Newsletter from the company, reported that Mr. Leroy Gabel, a farmer at Huntley in south-central Montana, first planted a Quantum wheat hybrid from HTSI seven years ago. Today he plants all 500 of his dryland acres in Quantum hybrids. HTSI made a summary over multi-years and multi-locations on experimental plots and farmer's field and concluded that wheat hybrids outyielded consistently 10–20% over conventional varieties. Therefore, it will be profitable to grow wheat hybrids if hybrid seed is produced economically.

Transgenic technology has been proposed to add a herbicide resistant gene in the wheat hybrid system (Gressel, 1996). The dominant resistant gene to a herbicide is integrated in the female parent. Then, the female parent and male parent can be planted in one sowing for easier outcrossing pollination, and the male parent is culled by herbicide after pollination is finished. The harvesting from the female parent plants left over after herbicide cleaning results in hybrid seeds.

There is an important assumption in this proposal, a complete male sterility for the female parent population. It is this assumption or requirement that wheat scientists from all over the world feel hopeless about after working on it for decades. The described difficulties above about the two extreme points of the genetic match in diploid rice and corn indicate the much more difficult situation in hexaploid wheat. Therefore, this proposal did not touch the essential barrier i.e. the two extreme points or the genetic conflict between male sterility and fertility. As to the outcrossing pollination, Chinese hybrid rice practice has proved that outcrossing pollination is effectively carried out even when the plant ratio of male to female is 1 to 10, or even 1 to 12.

Here we assume that the problem with the proposed wheat hybrid system is like the cytoplasmic male sterility in the current hybrid rice and in the past of hybrid corn. Integrating a herbicide resistant gene in the female parent can only eliminate the contaminations from male parent. In practice, the male parent is normal plant and only $\frac{1}{10}$ to $\frac{1}{12}$ of male parent population is needed in hybrid seed production system. The $\frac{1}{10}$ to $\frac{1}{12}$ of male parent population can be purified through roguing, especially in developing countries. On the other hand, all the contaminations from female parent side including incomplete male sterility due to genetic manipulation in cytoplasmic male sterile system, weather changes in the photoperiod and temperature sensitive male sterile system, and chemical rate or weather in chemically induced male sterile system plus natural mutants in female parent population can not be eliminated because the contaminating plants from all these sources have the resistance to its herbicide. Therefore, this proposal still requires the two extreme points of male sterility and fertility in crop hybrid system. In fact, mature male plants are very hard to be culled by the herbicide.

As a conclusion, this proposal of female resistance to herbicide has not caught the public attention because of the serious requirement of complete male sterility although it is helpful for developed countries to use machinery in crop hybrid system.

In accordance with the present invention, an improved chemically induced male sterile system can be commercialized. The improved CIMS does not have any conflicts of the two extreme points as well as the serious genetic match, and does not need a breeding program for male sterile female parent. The improved procedure is as follows.

A. A popular wheat cultivar with great general combining ability is chosen for male parent, and the dominant resistant gene to a herbicide is integrated into the male parent through either molecular transformation or hybridization transferring from a transgenic wheat material.

B. Test-crossing is conducted by using this male parent with many distant varieties to identify female parent through evaluating their hybrids for grain yield, stress tolerance, grain quality etc. breeding objectives.

C. Both the male and female parents are planted in the field in alternate rows.

D. Low rate of chemical for inducing male sterility (low enough not to cause female sterility and other physiological and morphological deformation, especially female sterility) is applied to the female parent at proper time, and pollination aid is conducted for maximum hybrid yield. Harvesting hybrid seed is only from the female parent. Here, partial fertility due to incomplete induction to male sterility is tolerable and seed yield of the hybridization is an important consideration. 80% induced male sterility or even lower is still workable.

E. Seed sample of the harvested hybrid seed is taken, and planted in a flat tray, and the seedlings are sprayed with the herbicide matched with the resistant gene. The seed purity is obtained by scoring dead plants (impure hybrid) and live plants (true hybrid) and labeled to the seed lot.

F. Based on plant density required, seed rate is calculated by the seed purity labeled before seeding in the field and the herbicide matched with the resistant gene on the field or otherwise is applied at 3–6 leaf stage for securing true hybrid population as well as weed control before fertilizer application.

A new area of chemically induced male sterility is needed for research—seed treatment. Straighthead, a physiological disease causing sterility of panicles so the panicles are erect, is popular in rice of the southern U.S. rice belt. Monosodium methanearsonate (MSMA) is publicly recognized as the chemical to evaluate this disease in the breeding program by applying it to the field before rice planting. This fact gives us a clue or good reason to conduct an extensive research for induced male sterility of female parent by seed treatment in the hybrid system. If it is successful, the induction procedure of male sterility will be simplified greatly and the hybrid seed cost will be reduced even more.

Meanwhile, the reduced genetic conflict between male sterility and fertility of the present invention provides an opportunity for wheat scientists to explore other male sterile cytoplasm other than *T. timopheevii*, the cytoplasm used popularly to produce complete male sterility.

Rice (*Oryza sativa* L.)

The present invention has an instant application in hybrid rice system through a transgenic male parent of a single gene for herbicide resistance.

In China and other Asian countries, the present invention will:

(1). Eliminate labor used for roguing in both cycles i.e. male sterile line self-reproduction and hybrid seed production, and save poor quality seeds of hybrid from destruction (hybrid seed with purity less than 96% is prohibited for commercializing in China).

(2). Commercialize diverse male sterile lines such as II-32A, You-1A, Ke-zhenA etc. to break down the genetic uniformity and increase genetic diversity and the yield of both hybrid seed production and $F_1$ hybrids.

(3). Replace CMS system with environmental male sterility (two line system) including PGMS or TGMS or P-TGMS by effectively eliminating false hybrids or contaminations due to male sterile instability from environmental variation. This will reduce production cost greatly because of the simplification in rice hybrid system.

(4). Enhance chemically induced male sterility (CIMS) so it can be commercialized by effective correction of incomplete male sterile induction. This will reduce production cost further because no breeding for male sterile female parent as in PGMS and TGMS system is needed in this system.

All these benefits will reduce production cost, increase the profit of production, which, in return, will enlarge rice hectarage and increase demand for herbicide supply in these countries.

In the U.S. and other developed countries, the present invention will:

Improve machinery operation and grain quality. These two major concerns in these countries decide the feasibility of two line system or CIMS only.

(1). Improved two line system: Rice Tech. Inc. in Texas has experimented with two line hybrid rice for years. Hybrid rice produced from this company has met quality requirement and contracted by consumer (F. Xie, personal comm.). However, seed purity of hybrid is the major barrier for its commercialization due to partial fertility from environmental (temperature) change. Using the present invention, Rice Tech. should be able to commercialize hybrid rice in the U.S. and other developed countries in 3–5 years.

(2). Improved CIMS: Grain quality of hybrid can be easily met in CIMS system. For example, Cypress and Litton are two standard long grain varieties, and have differences in genetic pedigree and geographic origin. Grain quality of hybrid from the two varieties is supposed to be a standard long grain also if heterosis is pronounced in this hybrid. Cypress is used as male parent since it has been transformed with resistant gene to herbicide Liberty, and Litton as female parent if an effective chemical for inducing male sterility is identified. The production procedure will be same as described in wheat by using Liberty. If Cypress is not tall enough for pollen dispersal to female panicle, the Liberty resistant gene can be transferred from Cypress to Kaybonnet by continuously backcrossing with Kaybonnet as the recurrent parent and offspring selection by spraying with Liberty. Then the resistant Kaybonnet can be used as male parent to mate with Litton. The same thing can be done between medium grain varieties, Liberty resistant Bengal and regular Orion. Research has been conducted on the application of CIMS in hybrid rice of China for decades, but further studies are still needed to identify effective chemicals and maturate the induction technology for male sterility. The chemicals identified by HybriTech to be applied to wheat can possibly be used with rice.

Corn (*Zea mays* L.)

Corn is cultivated on 130 million hectares in the world and 27 million hectares in the U.S. annually. Corn is the first grain crop in which heterosis utilization has been successfully commercialized through cytoplasmic male sterility. The two most commonly used methods of pollen control are detasseling and cytoplasmic male sterility. Detasseling currently represents the most widely used method of pollen control after the late 1970's due to leaf blight epidemics from cms-T. Detasseling involves the physical removal of the tassel from the female parent, either as a manual operation or in combination with mechanical devices. To ensure that each seed field meets the necessary quality (seed genetic purity) standards, tassels from the female parent rows must be removed before they shed pollen and/or before silks emerge on the ear shoots of the female parent. The operation is much more difficult when it is rainy or windy during tasseling or silking period. This is an expensive operation, costing the seed company from $250 to $320 per female hectare in the early 1990's for an average female parent. Increasing wage rates and deteriorating population demographics (labor supply and its distribution) are two factors that will continue to pose challenges to the industry.

Pioneer Hi-Bred Intl. reported experiment progress that transgenic technology was utilized in corn hybrid system (Songstad et al., 1997).

With the aid of the present invention, corn scientists are encouraged to go back to the cytoplasmic male sterility (CMS) system. When partial fertility of CMS lines is tolerable and normal fertility of $F_1$ hybrids is majorly considered, cms-C, cms-S and many other cms except cms-T can be utilized in the corn hybrid system. Then, there will be a good diversity of cms in the field and disease epidemics will be effectively prevented. Meanwhile, chemically induced male sterility needs to be studied in corn as described in wheat. Foliar application of the chemical is much easier in corn than in cereal crops. Third, environmental male sterility such as photo-genic male sterility (PGMS), thermo-genic male sterility (TGMS), and photo-thermo-genic male sterility (P-TGMS) as described in rice needs to be researched. Success in any one of these three areas combined with the present invention will release seed companies from labor intensive detasseling.

Rapeseed (*Brassica napus* L.)

The commercial potential of developing $F_1$ hybrids in rapeseed-mustard appears very promising, as hybrid yield advantages equal to or even greater than those in corn, millet and rice have been demonstrated (Banga, 1993).

Three major hybrid systems have been studied in this crop i.e. cytoplasmic male sterility (CMS) system including Raphanus-based CMS, Bronowski-Shiga-Thompson CMS, Polima CMS, Oxyrrhina CMS, etc., self-incompatibility system, and chemical induction MS system.

Several major chemical companies such as AgrEvo, Japan Tobacco, Pioneer, etc. are working on transgenic male sterility system (TMSS) on canola and other crops. Liberty Link and SeedLink project is an example of this system from AgrEvo (AgrEvo U.S.A. Inc., 1997). According to its newsletter, by using transgenic technology, male sterile gene is transferred to female parent, and male restoring gene to the sterility is transferred to male parent. It was stated that "Canola seed combined with Liberty Link and SeedLink has been successfully on the Canadian market since the autumn of 1996".

However, the present invention or technology is applicable economically to the three systems by transferring Liberty Link or Roundup Ready gene to a variety used as the male parent. This transgenic male parent can be used for all the three systems if it contains restoring gene to CMS lines and also is self-compatible.

(1). Improved cytoplasmic male sterile system: By reducing the conflict of the two extreme points between sterility and fertility, male sterile line with incomplete sterility in a low degree and strong combining ability is mated with the transgenic male parent. The $F_1$ field of production is sprayed with Liberty or Roundup to eliminate false hybrid and weeds for securing hybrid uniformity in the field at seedling stage as described in rice.

(2). Improved Self-incompatible system: The self-incompatible line can be multiplied by inducing self seed set through $CO_2$ treatment in adequately ventilated polythene tunnels. Self-incompatible lines can be sown alternating with the self-compatible transgenic pollinator to produce large quantities of hybrid seed containing the herbicide resistant gene from the pollinator. False hybrid plants due to incomplete self-incompatibility and weeds will be culled by spraying the herbicide on the field.

(3). Improved chemical hybridizing system: Any transgenic varieties can be used as male parent in this system. The technical procedure or methodology is same as described in wheat or rice.

Comparison of Transgenic Male Sterility System (TMSS) with Present Invention

The following are differences between TMSS from AgrEvo, Pioneer, Japan Tobacco, etc. as described above (AgrEvo U.S.A. Inc. 1997; DeBlock and Debrouwer, 1992; Denis et al., 1993; Mariani et al., 1990, 1992; Songstad et al., 1997) and the present invention.

(1). Number of genes: TMSS contains three genes i.e. herbicide resistance (bar) linked closely with male sterility (barnase) which requires a co-transformation processing to female parent (DeBlock and Debrouwer, 1991) and fertility restoration (barstar) to male parent. The present invention needs only one gene, herbicide resistance (bar) transferred to male parent. Gene transformation is the process in which a foreign gene is randomly inserted in a spot of DNA, and the original gene in that spot is replaced. Extensive selection on great amount of treated individuals identifies the individual in which an invisible or not important gene is replaced, i.e. the transgenic line appears exactly the same as its original plant except the new trait from the foreign gene. Two linked gene transformation to the female and one gene transformation to the male in the TMSS system will be much more difficult, complex and costly. Furthermore, the chance of success of TMSS will be greatly reduced by the difficulty and complexity. The single gene transformation of the present invention is advantageous over this point.

(2). Source and multiplication of male sterility: Two linked gene (bar and barnase) transformation is required to bring both male sterility and herbicide resistance into female parent in TMSS. Outcrossing of the transgenic female with regular or wild type plants to produce half male sterile plants maintains or multiplicates the female. The another half regular or wild offspring plants from the outcrossing are eliminated by spraying herbicide to the field of hybrid seed production or seed coating, which makes the male sterile female plants distribute very unevenly and limits the seed production of hybrid.

The present invention makes use of male sterilities accumulating from heterosis research for decades in the world, i.e. from all three hybrid systems used currently:

(A). CMS system: Male sterile cytoplasm is the source of male sterility, and the male sterility is multiplicated by its maintainer as the formate in hybrid rice, corn, rapeseed, etc.

(B). Environmental genic male sterile (EGMS) system: Male sterility is produced and multiplicated by environmental manipulation, i.e. plants are male sterile when they head in long-day period at high temperature (summer) for hybrid seed production, and male fertile when they head in short-day period at low temperature (autumn) for its multiplication. It was reported that remarkable progress of EGMS has been made in rice, wheat, corn, sorghum, rape, cotton, etc.

(C). Chemically induced male sterility (CIMS) system: Male sterility is produced by applying chemical hybridizing compound and multiplicated by not applying the compound, i.e. regular growth of the female.

(3). Flexibility of hybrid combination: In TMSS, the female parent is two linked gene transgenic, and the male parent is one gene transgenic. Any elite variety has to be transformed before chance of test-crossing with any member in the hybrid system before entry into the system is granted. In other words, wild lines including naturally male sterile lines can not be test-crossed with the male parent because they do not have herbicide resistant (bar) and transgenic male sterile (barnase) genes which are essential for the female in the hybrid system. Also, any wild lines can not be test-crossed with the female parent because they do not have restoring gene (barstar) to the transgenic male sterile female parent in the hybrid system. Obviously, choice of parent selection in the TMSS hybrid system is greatly limited.

In the present invention, only the male parent is single gene transgenic (bar), which indicates that there is no limitations at all for any female parent to get into the hybrid system other than current breeding objectives. On the other hand, any elite variety has to be transgenic right before formally entering the hybrid system as male parent. Before entering, test-crossing with the target female parent is conducted for satisfactory heterosis confirmation, so all the varieties are guaranteed for entering the hybrid system after its transgenic process. Actually, EGMS and CIMS are environmental and physiological male sterility, which means no specific restoring gene is required for restoring their fertility. Therefore, the elite transgenic male parent in CMS is also supposed to be elite in either EGMS or CIMS if the three systems exist together in the production. If only EGMS and CIMS are in the production, the elite transgenic male parent can be shared by each other. Generally, any new materials with good general combining ability from breeding program can be transgenic as potential male parent. A transgenic process can be done in about 3 years by continuously backcrossing with the new line that is used as recurrent parent and offspring selection based on herbicide resistance in most cases.

(4). Herbicide application: In TMSS, herbicide is applied to the field of female plants for getting rid of another half of male fertile plants in the population for hybrid seed production. However, in accordance with the present invention, herbicide is applied to the field of $F_1$ hybrid plants to secure hybrid uniformity by eliminating false hybrids from outcrossing with either intraline of female parent or contaminated male parent, and plants from selfing of the female because of incomplete male sterility due to MS cytoplasm in CMS, environmental variation in EGMS and incomplete induction in CIMS.

The present invention not only increases the effectiveness and reduces the cost of existing seed, crop, or plant heterosis, but also makes possible effective and economical commercial scale heterosis or hybridization of seeds, plants, or crops which before was impossible. Although the present invention is eloquently simple as described herein, it provides unexpected and heretofore unimaginable results such as reduced cost, reduced labor, increased production, increased purity, increased genetic diversity, increased hybrid vigor, increased use of heterosis or hybridization, and the like.

Figure 9:
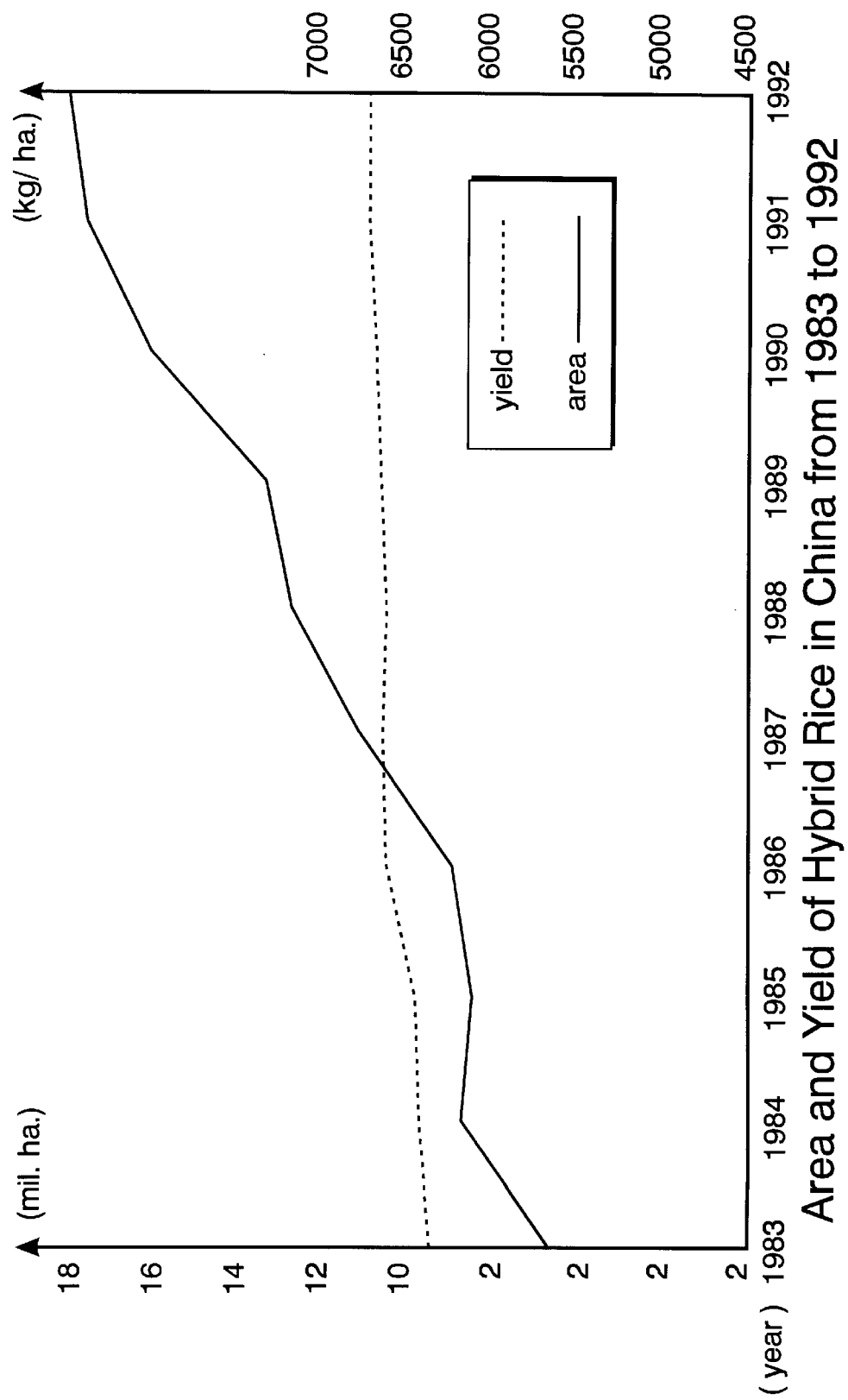
FIG. 9 is a graphical representation of area and yield of hybrid rice in China from 1983 to 1992.

With respect to FIG. 9 of the drawings, although hybrid rice research and development in the commercial utilization of heterosis and rice has made some advancements during the last 20 years, it is still in the juvenile stage and it appears that the yield potential of existing hybrid rice varieties has plateaued. In accordance with the present invention, the yield and hybrid vigor can be increased by having a broader selection of female parent or MS line and male parent varieties.

Figure 10:
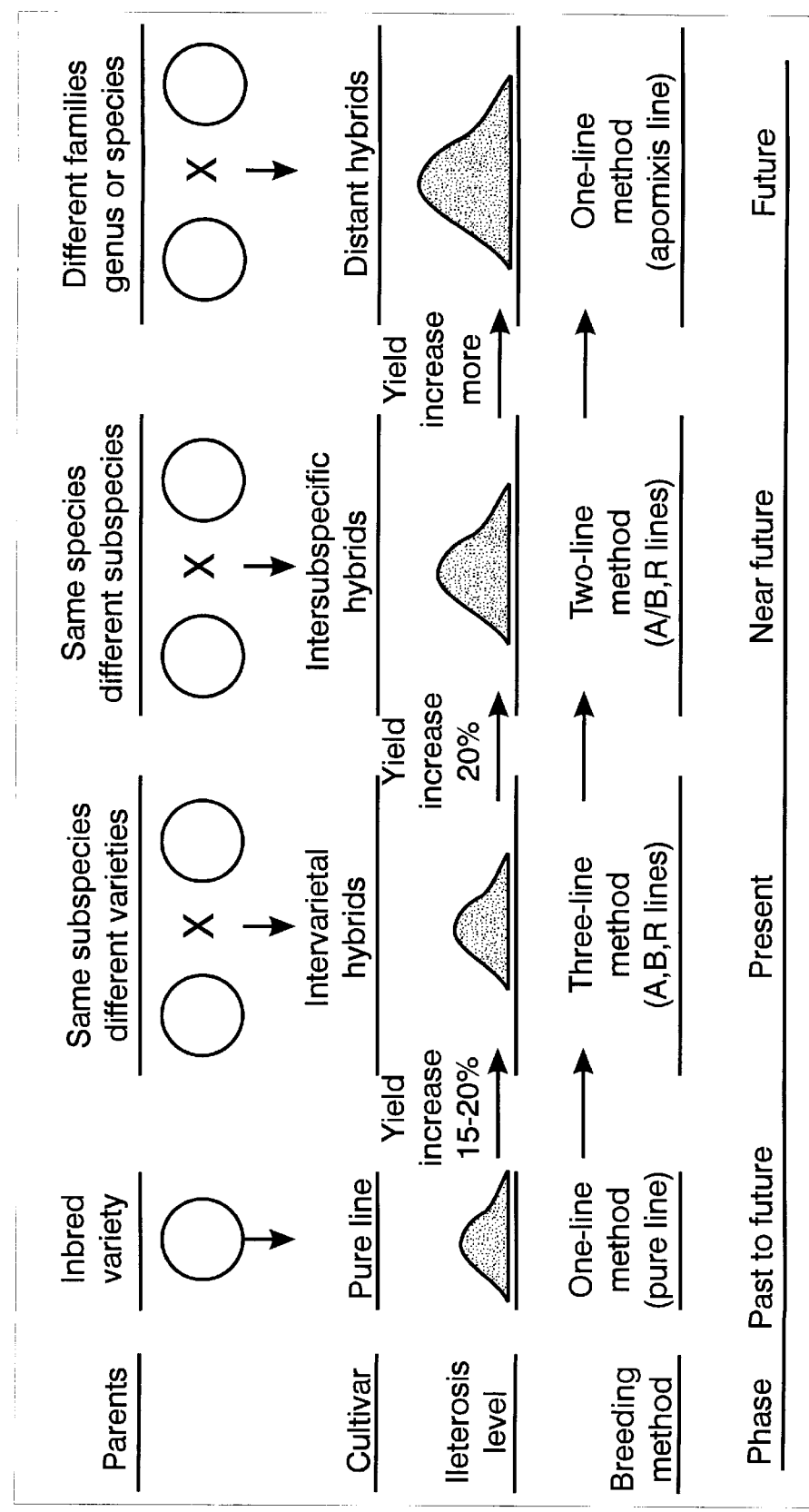
FIG. 10 is a schematic diagram of proposed development of hybrid rice breeding to increase rice yield.

As shown in FIG. 10 of the drawings, a comparison of different breeding methods and heterosis levels of rice is projected. In accordance with the present invention, distant hybrids having increased yield should be achievable.

Figure 11:
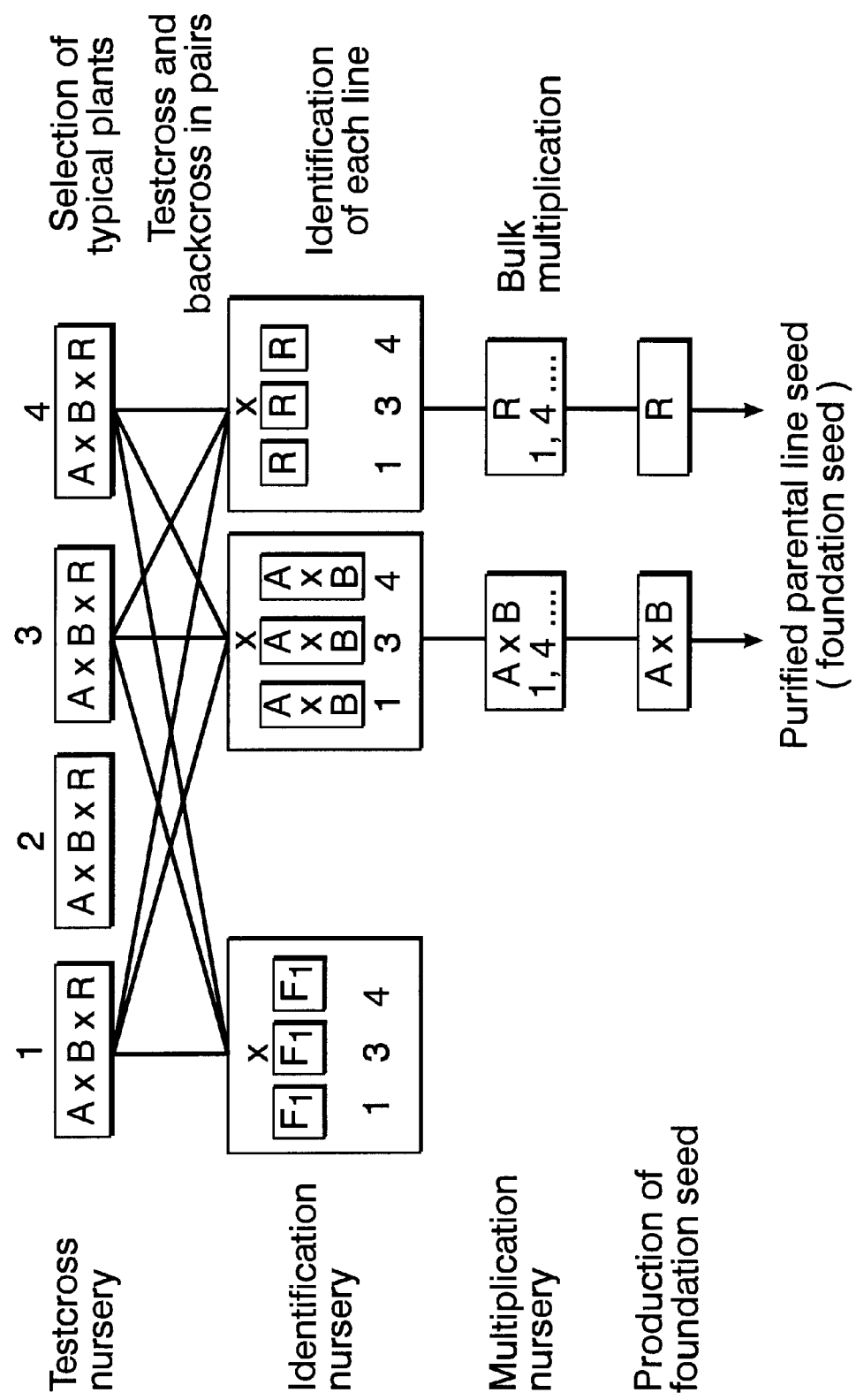
FIG. 11 is a schematic flow diagram of a procedure for purifying parental lines.

With respect to FIG. 11 of the drawings, one example of a procedure for purifing parental lines is shown. This example is directed to a conventional three parental line system. In accordance with the present invention, this procedure is simplified.

References

AgrEvo U.S.A. Inc. 1997. The Seed of success. Let's Grow, (the company's newsletter).

Ahrens, William H. 1994. Herbicide handbook. 7th edition. P. 147–149. Weed Sci. Soc. Amer. Champaign, Ill.

Baird, D. D., R. P. Upchurch, W. B. Homesley, and J. E. Franz. 1971. Introduction of a new broadspectrum postemergence herbicide class with utility for herbaceous perennial weed control. In Proceedings of the 26th North Central Weed Control Conference. P. 64–68. Champaign, Ill. Weed Science Society of Amercia.

Banga, S. S. 1993. Heterosis and its utilization. Monog. Theor. Appl. Genet. 19:21–43.

Bright, S. W. J.. 1992. Herbicide-resistant crops. P. 184–194. In "Biosynthesis and Molecular Regulation of Amino Acids in Plants". B. K. Singh, H. E. Flores, and J. C. Shannon (eds.). Amer. Soc. Plant Physiol., Rockville, Md.

Casas, A. M., A. K. Kononowiez, U. B. Zehr, D. T. Tomes, J. D. Axtell, L. G. Butler, R. A. Bressan, and P. M. Hasegawa. 1993. Transgenic sorghum plants via microprojectile bombardment. Proc. Natl. Acad. Sci., USA. 90:11212–11216.

Cheng, S. H., H. M. Si, L. S. Zhou, and Z. X. Sun. 1996. Classification of environmentally induced genetic male sterile lines of rice based on their fertility responses to photoperiod and temperature. J. of Agricultural Science. Cambridge, 127: 161–167.

Comai, L., L. C. Sen, and D. M. Stalker. 1983. An altered aroA gene product confers resistance to the herbicide glyphosate. Science 221:370–371.

Darwin, C. 1877. The effect of cross and self-fertilization in the vegetable kingdom. Dappleton, New York.

De Block, M., D. Debrouwer, and T. Tenning. 1989. Transformation of *Brassica napus* and *Brassica oleracea* using *Agrobacterium tumefaciens* and the expression of the bar and neo genes in the transgenic plants. Plant Physiol. 91: 694–701.

De Block, M., and D. Debrouwer. 1991. Two T-DNA's co-transformed into *Brassica napus* by a double *Agrobacterium tumefacines* infection are mainly integrated at the same locus. Theor. Appl. Genet., 82(3): 257–263.

De Block, M., and D. Debrouwer. 1993. Engineered fertility control in transgenic *Brassica napus* L.: Histochemical analysis of anther development. Planta, 189(2): 218–225.

Dekker, J., and G. Comstock. 1992. Ethical and environmental considerations in the release of herbicide resistant crops. Agricul. Hum. Values. 9(3), 31–43.

Dekker, J., and S. O. Duke. 1995. Herbiside-resistant field crops. P. 69–116. In "Advances in Agronomy". Donald L. Sparks (ed.). Vol. 54. Academic Press, Inc.. Harcourt Brace & company. San Diego, New Yoark, etc..

Denis, M., R. Delourme, J. P. Gourret, C. Mariani, and M. Renard. 1993. Expression of engineered nuclear male sterility in Brassica napus: genetic, morphology, cytology, and sensitivity to temperature. Plant Physiol., vol. 101 (4): 1295–1304.

Devine, M. D., S. O. Duke, and C. Fedtke. 1993. Physiology of herbicide action. Prentice Hall, Englewood Cliffs, N.J.

Duke, S. O. 1988. Glyphosate. P. 1–70. In "Herbicide, Chemistry, Degradation, and Mode of Action". P. C. Kearney and D. D. Kaufman (eds.). Vol. III. Dekker, New York.

Duke, S. O. 1996. Herbicide resistant crops. P. 1–10. Lewis Publishers, Boca Raton, etc.

Dyer, W. E.. 1994. Resistance to glyphosate. P.229–241. In "Herbicide Resistance in Plants". S. B. Powles and J. A. M. Holtum (eds.). Lewis Publishers, Boca Raton, Ann Arbor, London, Tokyo.

Dyer, W. E., F. D. Hess, J. S. Holt, and S. O. Duke. 1993. Potential benefits and risks of herbicide-resistant crops produced by biotechnology. Hortic. Rev. 15:367.

Frankel, R. and E. Galum. 1977. Pollination mechanism, reproduction and plant breeding. Springer-Verlag, Berlin Herdelberg, New York.

Franz, J. E.. 1985. Discovery, development and chemistry of glyphosate. P. 3–17. In "The Herbicide of Glyphosate". E. Grossbard and D. Atkinson (eds.). London, Butterworths.

Gianessi, L. P., and C. Puffer. 1991. Herbicide use in the United States. Resources for the Future. Washington, D.C.

Goldburg, R. J., J. Rissler, H. Shand, and C. Hassebrook. 1990. Biotechnology's bitter harvest: herbicide tolerant crops and the threat to sustainable agriculture. Environmental Defense Fund, City of New York.

Gravois, K. A., K. A. K. Moldenhauer, F. L. Baldwin and S. D. Linscombe. 1997. Evaluation of Liberty-resistant rice in Arkansas. P. 12–16. In "Rice Research Studies". R. J. Norman and T. H. Johnston (eds.). Arkansas Agri. Exp. Sta.. Research Series 456.

Gressel, J. 1996. The potential roles for herbicide-resistant crops in world agriculture. p. 231–250. In Herbicide-resistant crops. Stephen O. Duke (ed.) CRC Lewis Publishers, Boca Raton, New York, London, Tokyo.

Grossbard, E., and D. Atkinson. 1985. The herbicide glyphosate. Butterworths. London.

HybriTech. 1997. Hybrids gain consultants' approval—Bringing new energy to wheat. Waves (the company's newsletter: Quantum-Hybrid wheat). Spring, 1997

Jan, C. C., and J. N. Rutger. 1988. Mitomycin C- and streptomycin-induced male sterility in cultivated sunflower. Crop Sci. 28: 792–795.

Laursen, C. M., R. A. Krzyzek, C. E. Flick, P. C. Anderson, and T. M. Spencer. 1994. Production of fertile transgenic maize by electroporation of suspension culture cells. Plant Mol. Biol. 24:51–61.

Linscombe, S. D., P. Christou, F. Jodari, J. H. Oard, M. P. Braverman, R. S. Helms, D. L. Jordan, D. E. Sanders, and W. C. Rice. 1996. Review of research with transgenic glufosinate resistant rice lines. P. 59. Proc. of the 26th RTWG (rice technical working group). San Antonio, Tex. Feb. 25–28, 1996.

Lou,Xizhi and C. X. Mao. 1994. Hybrid rice in China—A success story. Asia-Pacific Association of Agricultural Research Institutions, FAO Reginal Office for Asia & the Pacific, Bangkok.

Malik, J., G. Barry, and G. Kishore. 1989. The herbicide glyphosate. BioFactors. 2:17–25.

Mao, C. X. 1994. Hybrid rice production in China. Paper presented at the 'Hybrid rice working group for Latin America'. Goiania, Brazil. Mar. 16–18, 1994.

Mariani, C., M. De Beuckeleer, J. Truettver, J. Leemans, and R. B. Goldberg. 1990. Induction of male sterility in plants by a chimaeic endonuclease gene. Nature (London). 347: 737–741.

Mariani, C., V. Gossele, M. De Beuckeleer, M. De Block, R. B. Goldberg, W. De Greef, and J. Leemans. 1992. A chimaeric ribonuclease-inhibitor gene restores fertility to male sterile plants. Nature (London). 357: 384–387.

Mendel, G.. 1865. Versuche uber Pfflanzen hybriden. Naturuf. Ver in Brunn. Ver. 4: 3–47.

Miller, M.. 1991. The promise of biotechnology, developing pesticide- and herbicide-resistant crops. J. Environ. Health 54(2), 13–14.

Mullner, H., P. Eckes, and G. Donn. 1993. Engineering crop resistance to the naturally occurring glutamine synthetase inhibitor phosphinothricin. ACS Symp. Ser. 524, 38–47. Amer. Chem. Soc., Washington, D.C.

Padgette, S. R., G. Della-Cioppa, D. M. Shah, R. T. Fraley, and G. M. Kishore. 1989. Selective herbicide tolerance through protein engineering. P. 441–476. In Cell Culture and Somatic Cell Genetics of Plants. J. Schell and I. Vasil (eds.), Vol. 6. Academic Press, New York.

Pilmoor, J. B., S. D. Lindell, G. G. Briggs and K. Wright. 1995. Procedings in Eighth International Congress of Pesticide Chemistry, Options 2000. P. 292–303. N. N. Ragsdale, P. C. Kearney, and J. R. Plimmer (eds.). American Chemical Society. Washington, D.C.

Rathmore, K. S., V. K. Chowdhury, and T. K. Hodges. 1993. Use of bar as a selectable marker gene and for the production of herbicide-resistant rice plants from protoplasts. Plant Mol. Biol. 21: 871–884.

Rhodes, D., G. C. Ju, W. J. Yang, and Y. Samaras. 1992. Plant metabolism and heterosis. In "Plant Breeding Reviews". Janick, J (ed.),10: 53–91, Springer-Verlag, Berlin, Herdelberg, New York.

Rominger, R.. Deputy Secretary of U.S. Department of Agriculture. 1997. Speech on California Council on Science and Technology, Uni. of Cali., Riverside. Nov. 18, 1997. USDA Release No.0408.97.

Shah, D. M., R. B. Horsch, H. J. Klee, G. M. Kishore, J. A. Winter, N. E. Tumer, C. M. Hironaka, P. R. Sanders, C. S. Gasser, S. A. Aykent, N. R. Siegel, S. G. Rogers, and R. T. Fraley. 1986. Engineering herbicide tolerance in transgenic plants. Science. 233:478–481.

Shull, G. H.. 1908. The composition of a field of maize. Amer. Breed. Assoc. Rep. 4: 296–301.

Songstad, D. D., S. J. Corak, M. C. Albertsen, M. Trimnell and S. Nelson (Pioneer Hi-Bred Intl.). 1997. Use of herbicide seed-coating to maintain male sterile maize plants. Agronomy Abstract, p. 150. Annual Meeting, American Society of Agronomjy, Anaheim, Calif., Oct. 26–31, 1997

Stalker, D. M., J. A. Kiser, G. Baldwin, B. Coulombe, and C. M. Houck. 1996. Cotton weed control using the BXN™ system. P. 93–105. In "Herbicide-resistant Crops". Stephen O. Duke (ed.). CRC Lewis Publishers, Boca Raton, New Roek, London, Tokyo.

Stuber, C. W. 1994. Heterosis in plant breeding. In "Plant Breeding Reviews". Janick, J (ed.), 12: 227–251, Springer-Verlag, Berlin, Herdelberg, New York.

Ullstrup, A. J. 1972. The impacts of the Southern corn leaf blight epidemics of 1970–1971. Ann. Rev. Phytopathol. 10:37–50.

Vasil, V., A. M. Castillo, M. E. Fromm, and I. K. Vasil. 1993. Herbicide resistant fertile transgenic wheat plants obtained by microprojectile bombardment of regenerable embryonic callus. Biotechnology. 10: 667–674.

Vasil, I. K.. 1994. Phosphinothricin-resistant crops. In "Herbicide-resistant Crops: Agricultural, Environmental, Economic, Regulatory, and Technical Aspects". S. O. Duke (ed.). Lewis Publishers, Chelsea, Mich.

Vasil, I. K.. 1996. Phosphinothricine-resistant crops. P85–91. In "Herbicide-resistant Crops". Stephen O. Duke (ed.). CRC Lewis Publishers, Boca Raton, New York, London, Tokyo.

Virmani, S. S.. 1985. Use of male sterility in crop improvement. In "Genetic Manipulation for Crop Improvement". Chopra (ed.). Oxford and Indian Book House, New Delhi.

Virmani, S. S.. 1994. Heterosis and hybrid rice breeding. Monogr. Theor. Appl. Genet. 22. Springer-Verlag.

Wan, Y., and P. G. Lemaux. 1994. Generation of large numbers of independently transformed fertile barley plants. Plant Physiol. 104: 37–48.

Weeks, J. T., O. D. Anderson, and A. E. Blechl. 1993. Rapid production of multiple independent lines of fertile transgenic wheat (*Triticum aestivum*). Plant Physiol. 120: 1077-.

Wheeler, C., F. Baldwin, D. Gealy, and K. Gravois. 1997. Weed control in Liberty-tolerant rice. P. 64–66. In "Rice Research Stidies". R. J. Norman and T. H. Johnston (eds.). Arkansas Agri. Exp. Sta.. Research Series 456.

Williams, M. E., and C. S. Levings III. 1992. Molecular biology of cytoplasmic male sterility. In: Janick, J(ed.), Plant Breeding Reviews 10: 23–51, Springer-Verlag, Berlin, Herdelberg, New York.

Yuan, L. P., Z. Y. Yang, and J. B. Yang. 1992. Hybrid rice in China. Paper presented at the 2nd Int. Symp. on Hybrid Rice. IRRI, Manila, Philippines. Apr. 21–25, 1992.

Yuan, L. P., and X. Q. Fu. 1995. Technology of hybrid rice production. Food and Agriculture Organization of the United Nations, Rome.

TABLE 1

Annual Hybrid Rice Growing Area and its Percentage to Total Rice Area in China

| Year | Hybrid rice growing area (Million hectars) | Percentage to total area (%) |
|---|---|---|
| 1980 | 4.79 | 14.4 |
| 1981 | 5.11 | 15.4 |
| 1982 | 5.62 | 17.0 |
| 1983 | 6.75 | 20.4 |
| 1984 | 8.85 | 26.7 |
| 1985 | 8.61 | 26.9 |
| 1986 | 9.56 | 29.6 |

TABLE 1-continued

Annual Hybrid Rice Growing Area and its Percentage to Total Rice Area in China

| Year | Hybrid rice growing area (Million hectars) | Percentage to total area (%) |
|---|---|---|
| 1987 | 10.97 | 34.1 |
| 1988 | 13.33 | 41.7 |
| 1989 | 13.33 | 40.8 |
| 1990 | 16.65 | 50.3 |
| 1991 | 17.64 | 54.1 |

Source: Chinese Academy of Agricultural Sciences (CAAS), 1992

TABLE 2

Yield Increase of Hybrid Rice over Conventional Rice in China

| Year | Hybrid Rice (Kg/ha) | Conventional Rice (Kg/ha) | Yield Increase of Hybrid (%) |
|---|---|---|---|
| 1980 | 5296.5 | 2940.5 | 34.4 |
| 1981 | 5310.0 | 4113.0 | 29.3 |
| 1982 | 5865.0 | 4447.5 | 31.9 |
| 1983 | 6375.0 | 4774.5 | 33.5 |
| 1984 | 6405.0 | 4992.0 | 28.2 |
| 1985 | 6472.5 | 4815.0 | 34.4 |
| 1986 | 6600.0 | 4857.0 | 35.9 |
| 1987 | 6615.0 | 4779.0 | 38.4 |
| 1988 | 6600.0 | 4539.0 | 45.4 |
| 1989 | 6615.0 | 4534.5 | 45.9 |
| 1990 | 6675.0 | 4642.5 | 43.8 |
| 1991 | 6660.1 | 4537.5 | 46.8 |

Source: Chinese Academy of Agricultural Sciences (CAAS), 1992

TABLE 3

Criteria of Seed Quality for Parental Lines and Hybrid

| Line | Grade | Purity >= (%) | Cleanliness >= (%) | Germination >= (%) | Moisture <(%) | Weeds <(g/kg) |
|---|---|---|---|---|---|---|
| A line | Foundation seed | 99.9 | 99.0 | 90.0 | 13.0 | 0 |
|  | 1st class | 99.5 | 99.0 | 90.0 | 13.0 | 0 |
| (CMS line) | 2nd class | 99.0 | 97.0 | 85.0 | 13.0 | 5 |
| B line | Foundation seed | 99.9 | 99.0 | 96.0 | 13.0 | 0 |
|  | 1st class | 99.5 | 99.0 | 96.0 | 13.0 | 0 |
| (Maintainer) | 2nd class | 99.0 | 97.0 | 93.0 | 13.0 | 5 |
| R line | Foundation seed | 99.8 | 99.0 | 96.0 | 13.0 | 0 |
|  | 1st class | 99.5 | 99.0 | 96.0 | 13.0 | 5 |
| (Restorer) | 2nd class | 99.0 | 97.0 | 93.0 | 13.0 | 5 |
| F1 | 1st class | 98.0 | 98.0 | 93.0 | 13.0 | 0 |
| Hybrid | 2nd class | 96.0 | 97.0 | 90.0 | 13.0 | 5 |

FIG. 7. Transgenic Gulfmont with Liberty Link gene pollinated Ce-64, a regular rice cultivar. Liberty (glufosinate) was sprayed 30 days after planting at 1.0 lb a.i. (active ingredient)/acre. The photo was taken 9 days after spraying Liberty. 70 plants of female parent Ce-64 died completely. 58 plants of male parent Gulfmont and 35 plants of $F_1$ hybrid from crossing of female Ce-64 with male Gulfmont were alive. This is a demonstration that dominant gene to Liberty resistance was transferred to $F_1$ hybrid through pollination from transgenic male parent.

FIG. 8. Transgenic Cypress PB-6 with Liberty Link gene pollinated Ce-64, a regular rice cultivar. Liberty (glufosinate) was sprayed 30 days after planting at 1.0 lb a.i. (active ingredient)/acre. The photo was taken 9 days after spraying Liberty. 70 plants of female parent Ce-64 died completely. 58 plants of male parent Cypress PB-6 and 35 plants of $F_1$ hybrid from crossing of female Ce-64 with male Cypress PB-6 were alive. This is a demonstration that dominant gene to Liberty resistance was transferred to $F_1$ hybrid through pollination from transgenic male parent.

Thus, it will be appreciated that as a result of the present invention, a highly effective improved seed, crop, or plant heterosis or hybridization system, method, protocol, process, or the like is provided by which the principal objective, among others is completely fulfilled. It is contemplated, and will be apparent to those skilled in the art from the preceding description and accompanying drawings, that modification and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

What is claimed is:

1. A hybridizing method of producing true hybrid seeds or plants, and preventing contamination from the female parental line by using a female parent which is male sterile and is not resistant to at least one selected non-selective herbicide and a male parent which is male fertile and is resistant to the at least one selected non-selective herbicide, comprising the steps of:

crossing a male parent which is male fertile, has at least one dominant nuclear gene which is resistant to at least one selected non-selective herbicide, and is resistant to the at least one selected non-selective herbicide, with a female parent which is substantially male sterile, does not include said at least one gene which is resistant to the at least one selected non-selective herbicides and is not resistant to the at least one selected non-selective herbicide, and harvesting seeds from the female parent which contain pure hybrid seeds having the herbicide resistant gene from the male parent and non-pure hybrid seeds, wherein said pure hybrid seeds produce plants which are resistant to the at least one selected non-selective herbicide and the non-pure hybrid seeds produce plants which are not resistant to the at least one selected non-selective herbicide spraying the hybrid population of the herbicide resistant male parent and the nonresistant female parent with the selected herbicide for hybrid purity control and weed control.

2. A hybridizing method of producing true hybrid seeds or plants and preventing contamination from the female parental line by using a female parent which is male sterile and is not resistant to at least one selected non-selective herbicide and a male parent which is male fertile and is resistant to the at least one selected non-selective herbicide, comprising the steps of:

crossing a male parent which is male fertile, has at least one dominant nuclear gene which is resistant to at least one selected non-selective herbicide, and is resistant to the at least one selected non-selective herbicide, with a female parent which is substantially male sterile, does not include said at least one gene which is resistant to the at least one selected non-selective herbicide, and is not resistant to the at least one selected non-selective herbicide, harvesting seeds from the female parent which contain pure hybrid seeds having the herbicide resistant gene from the male parent and non-pure hybrid seeds, wherein said pure hybrid seeds produce plants which are resistant to the at least one selected non-selective herbicide and the non-pure hybrid seeds produce plants which are not resistant to the at least one selected non-selective herbicide, and planting a portion of said harvested seeds and spraying or treating at least one of the plants from said seeds with at least said one selected non-selective herbicide to kill all weeds or plants which are not pure hybrids to determine the proportion of seeds which are pure hybrids.

3. A hybridizing method of producing true hybrid seeds or plants and preventing contamination from the female parental line by using a female parent which is male sterile and is not resistant to at least one selected non-selective herbicide and a male parent which is male fertile and is resistant to the at least one selected non-selective herbicide, comprising the steps of:

crossing a male parent which is male fertile, has at least one dominant nuclear gene which is resistant to at least one selected non-selective herbicide, and is resistant to the at least one selected non-selective herbicide, with a female parent which is substantially male sterile, does not include said at least one gene which is resistant to the at least one selected non-selective herbicide, and is not resistant to the at least one selected non-selective herbicide, harvesting seeds from the female parent which contain pure hybrid seeds having the herbicide resistant gene from the male parent and non-pure hybrid seeds, wherein said pure hybrid seeds produce plants which are resistant to the at least one selected non-selective herbicide and the non-pure hybrid seeds produce plants which are not resistant to the at least one selected non-selective herbicide, and planting or sowing the harvested seeds, and spraying or treating the weeds or plants, which grow from said harvested seeds to kill all non-pure hybrid plants and weeds and thereby leaving only pure hybrid plants to grow and be harvested.

4. The method as recited in claim 1, wherein said seed or plant is selected from the group of rice (*Oryza sativa* L.), wheat (*Triticum aestivum* L.), corn (*Zea mays* L.), cotton (*Gossypium hirsutum* L.), soybean (*Glycine max* L.), sorghum [*Sorghum bicolor*(L.) Moench], rapeseed (*Brassica napus* L.), barley (*Hordeum vulgare* L.), oat (*Avena sativa* L.), rye (*Secale cereale* L.), pearl millet [*Pennisetum typhoides* (Burm) Stspf et Hubb.], alfalfa (*Medicago sativa* L.), tomato (*Lycopersicon esculentum* L.), sugar beet (*Beta vulgaris* L.), sunflower (*Helianthus annuus* L.), onion (*Allium cepa* L.), petunia (*Petunia hybrida* Hort.), and carrot (*Daucus carota* L.).

5. The method as recited in claim 1, wherein said male parent has at least one dominant nuclear gene which is resistant to at least one non-selective herbicide selected from the group of glufosinate, glyphosate, and combinations thereof.

6. The method as recited in claim 1, wherein said harvested seeds are treated with the non-selective herbicide.

7. The method as recited in claim 3, further comprising the steps of:

spraying or treating the hybrid plants or crops at least one additional time to kill all non-pure hybrids and weeds. thereof.

8. The method as recited in claim 1, wherein said method is an improved heterosis or hybridization process for producing hybrid seeds or plants.

9. The method as recited in claim 1, wherein said method increases genetic diversity in hybrid seeds or plants.

10. An improved heterosis or hybridization process, comprising the steps of:

planting a male parent which is male fertile and has at least one dominant nuclear gene which is resistant to at least one selected herbicide, planting a female parent which is substantially male sterile and does not include said at least one gene which is resistant to the at least one selected herbicide, crossing the male parent with the female parent, and harvesting seeds from the female parent which contain pure hybrid seeds having the herbicide resistant gene from the male parent and non-pure hybrid seeds which do not have the herbicide resistant gene wherein spraying the hybrid population of the herbicide resistant male parent and the nonresistant female parent with the selected herbicide results in hybrid purity control and weed control.

11. The improved heterosis process of claim 10, further comprising the steps of:

spraying or treating plants produced from said harvested seeds with the selected herbicide to kill all weeds and non-pure hybrids.

12. In a CMS system, the improvement comprising the steps of:

using a male restorer or R line which is male fertile and contains at least one dominant nuclear gene which is resistant to at least one herbicide and using a female parent which is male sterile and does not contain said at least one gene which is resistant to the at least one herbicide wherein spraying the hybrid population of the herbicide resistant male parent and the nonresistant female parent with the selected herbicide results in hybrid purity control and weed control.

13. The improved CMS system of claim 12, further comprising the steps of:

spraying or treating seeds or plants produced from said system with the selected herbicide to kill all weeds and non-pure hybrids.

14. In an EGMS system, the improvement comprising the steps of:

using a male parent which is male fertile and contains at least one dominant nuclear gene which is resistant to at least one herbicide and using a female parent which is male sterile and does not contain said at least one gene which is resistant to the at least one herbicide wherein spraying the hybrid population of the herbicide resistant male parent and the nonresistant female parent with the selected herbicide results in hybrid purity control and weed control.

15. The improved EGMS system of claim 14, further comprising the steps of:
spraying or treating seeds or plants produced from said system with the selected herbicide to kill all weeds and non-pure hybrids.

16. In a CIMS system, the improvement comprising the steps of:
using a male parent which is male fertile and contains at least one dominant nuclear gene which is resistant to at least one herbicide and using a female parent which is male sterile and does not contain said at least one gene which is resistant to the at least one herbicide wherein spraying the hybrid population of the herbicide resistant male parent and the nonresistant female parent with the selected herbicide results in hybrid purity control and weed control.

17. The improved CIMS system of claim 16, further comprising the steps of:
spraying or treating seeds or plants produced from said system with the selected herbicide to kill all weeds and non-pure hybrids.

18. A novel protocol for the application of non-selective herbicide with its resistant gene in hybrid seed production utilizing heterosis or hybridization, comprising the steps of:
integrating a dominant nuclear herbicide resistant gene to at least one selected herbicide into a male fertile male parent to produce a herbicide resistant male parent;
pollinating a male sterile female parent which does not have said herbicide resistant gene and which is non-resistant to the at least one selected herbicide with the pollen of the herbicide resistant male parent; and,
spraying the hybrid population from the herbicide resistant male parent and the non-resistant female parent with the selected herbicide for hybrid purity control and weed control.

19. The protocol of claim 18, wherein the protocol is used in connection with at least one of the following plants selected from the group of rice (*Oryza sativa* L.), wheat (*Triticum aestivum* L.), corn (*Zea mays* L.), cotton (*Gossypium hirsutum* L.), soybean (*Glycine max* L.), sorghum [*Sorghum bicolor* (L.) Moench], rapeseed (*Brassica napus* L.), barley (*Hordeum vulgare* L.), oat (*Avena sativa* L.), rye (*Secale cereale* L.), pearl millet [*Pennisetum typhoides* (Burm) Stspf et Hubb.], alfalfa (*Medicago sativa* L.), tomato (*Lycopersicon esculentum* L.), sugar beet (*Beta vulgaris* L.), sunflower (*Helianthus annuus* L.), onion (*Allium cepa* L.), petunia (*Petunia hybrida* Hort.), and carrot (*Daucus carota* L.).

20. An improved hybridization process for the efficient production of hybrid seeds with security of hybrid purity in the field for all plants capable of having incomplete male sterility for female plants, which increases genetic diversity of the CMS system (many male sterile lines that are not absolutely male sterile can be used), which simplifies the procedure of hybrid seed production (using environmental genetic male sterility or chemically induced male sterility instead of cytoplasmic male sterility), and which utilizes heterosis more effectively and economically, comprising the steps of:
integrating a dominant nuclear resistant gene to a type of non-selective herbicide into a cultivar of at least one plant which will be used as male parent in a heterosis process, and multiplying this male parent as many times as necessary for seed demand,
pollinating a male sterile female population which does not include said resistant gene to the type of non-selective herbicide with the pollen of the male parent,
harvesting hybrid seeds from the female plant population,
planting the hybrid seeds for hybrid plants and spraying the hybrid seedlings with the type of non-selective herbicide matched to the integrated resistant gene to kill all the false hybrid plants, all false hybrid plants are eliminated because all of the false hybrid plants do not have the resistant gene to the type of non-selective herbicide, conversely, all the true hybrid plants do not suffer from the type of non-selective herbicide because they have the resistant gene transferred from the true male parent through pollination and because the resistant gene to the herbicide is inherited as a simple dominant allele, herbicide is sprayed on the production field directly for most plants, to kill any false hybrid plants in the hybrid population and any weeds in the field at same time, and
spraying the field with the type non-selective herbicide any time during the season for weed control as necessary.

21. The method as recited in claim 1, wherein said female parent is made male sterile using CMS.

22. The method as recited in claim 1, wherein said female parent is made male sterile using EGMS.

23. The method as recited in claim 1, wherein said female parent is made male sterile using CIMS.

24. The method as recited in claim 1, wherein said female parent is made male sterile by at least one of CMS, EGMS, CIMS, or combinations thereof.

25. The method as recited in claim 1, wherein said female parent is an A line and said male parent is a restorer line of a three line system.

26. The method as recited in claim 1, wherein said male and female parents form a two line system.

27. The method as recited in claim 1, wherein said female parent may not be sprayed with the at least one selected non-selective herbicide as the female parent is not resistant and would be destroyed, while the male parent population may be sprayed with the at least one selected non-selective herbicide for weed control.

28. The method as recited in claim 1, wherein said dominant nuclear gene which is resistant to the at least one selected non-selective herbicide is a single dominant allele.

29. A system of producing true hybrid rice seeds or plants, and preventing contamination from the female parental line by using a female parent which is male sterile and is not resistant to at least one selected non-selective herbicide and a male parent which is male fertile and is resistant to the at least one selected non-selective herbicide comprising the steps of:
crossing a male parent which is male fertile, has at least one dominant nuclear gene which is resistant to at least one selected non-selective herbicide, and is resistant to the at least one selected non-selective herbicide,
with a female parent which is substantially male sterile, does not include said at least one gene which is resistant to the at least one selected non-selective herbicide, and is not resistant to the at least one selected non-selective herbicide, and harvesting rice seeds from the female parent which contain pure hybrid seeds having the herbicide resistant gene from the male parent and non-pure hybrid seeds, wherein said pure hybrid seeds produce plants which are resistant to the at least one selected non-selective herbicide and the non-pure hybrid seeds produce plants which are not resistant to the at least one selected non-selective herbicide.

* * * * *